(12) United States Patent
Hoyt

(10) Patent No.: US 7,477,931 B2
(45) Date of Patent: Jan. 13, 2009

(54) SYSTEMS AND METHODS FOR IN-VIVO AND OPTICAL IMAGING AND MEASUREMENT

(75) Inventor: Clifford C. Hoyt, Wellesley, MA (US)

(73) Assignee: Cambridge Research & Instruments, Inc., Woburn, MA (US)

( * ) Notice: Subject to any disclaimer, the term of this patent is extended or adjusted under 35 U.S.C. 154(b) by 262 days.

(21) Appl. No.: 11/295,140

(22) Filed: Dec. 6, 2005

(65) Prior Publication Data

US 2006/0146346 A1    Jul. 6, 2006

Related U.S. Application Data

(60) Provisional application No. 60/633,511, filed on Dec. 6, 2004, provisional application No. 60/702,925, filed on Jul. 27, 2005, provisional application No. 60/707,497, filed on Aug. 11, 2005, provisional application No. 60/634,154, filed on Dec. 8, 2004, provisional application No. 60/720,080, filed on Sep. 23, 2005, provisional application No. 60/697,617, filed on Jul. 8, 2005.

(51) Int. Cl.
   *A61B 6/00* (2006.01)
(52) U.S. Cl. ...................................... 600/476
(58) Field of Classification Search ................ 600/431, 600/407, 312, 476, 425; 356/317, 318; 250/458; 382/128; 378/4, 6

See application file for complete search history.

(56) References Cited

U.S. PATENT DOCUMENTS

2004/0021771 A1    2/2004 Stearns et al.
2005/0065440 A1    3/2005 Levenson

FOREIGN PATENT DOCUMENTS

WO    WO 2005/040769    5/2005

OTHER PUBLICATIONS

Bevilacqua, F. et al., "Broadband absorption spectroscopy in turbid media by combined frequency-domain and steady-state methods", Applied Optics 39: 6498-6507 (2000).
Chalfie, M. et al., "Green Fluorescent Protein as a Marker for Gene Expression", Science 263: 802-805 (1994).
Chaudhari, A.J. et al., "Hyperspectral and multispectral bioluminescence optical tomography for small animal imaging", Physics in Medicine and Biology 50: 5421-5441 (2005).
Cuccia, D.J. et al., "Modulated imaging: quantitative analysis and tomography of turbid media in the spatial-frequency domain", Optics Letters 30: 1354-1356 (2005).
Diehn, F.E. et al., "Noninvasive Fluorescent Imaging Reliably Estimates Biomass In Vivo", BioTechniques 33: 1250-1255 (2002).

(Continued)

*Primary Examiner*—Eric F Winakur
*Assistant Examiner*—Lawrence N Laryea
(74) *Attorney, Agent, or Firm*—FIsh & Richardson P.C.

(57) ABSTRACT

Disclosed are methods and systems for: collecting radiation emitted from an object embedded in a biological sample from multiple sides of the sample; and estimating the size of the object based on the collected radiation.

38 Claims, 16 Drawing Sheets

OTHER PUBLICATIONS

Gao, X. et al., "In vivo cancer targeting and imaging with semiconductor quantum dots", Nature Biotechnology 22: 969-976 (2004).

Lightools Research, "Pan-A-See-Ya Panoramic Imaging System", downloaded from internet address http://www.lightools.com/LRTPDFS/panaseeypdf.pdf on Dec. 6, 2005.

Liu, Q. et al., "Experimental validation of Monte Carlo modeling of fluorescence in tissues in the UV-visible spectrum", Journal of Biomedical Optics 8: 223-236 (2003).

Troy, T.L. et al., "Optical properties of human skin in the near infrared wavelength range of 1000 to 2200 nm", Journal of Biomedical Optics 6: 167-176 (2001).

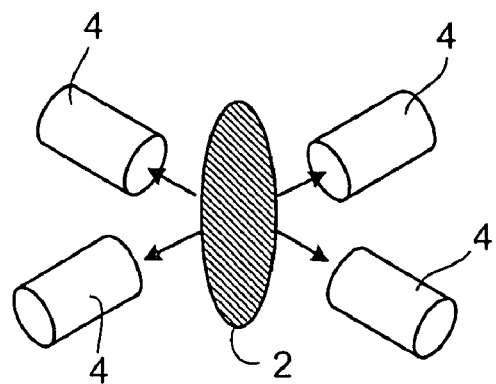
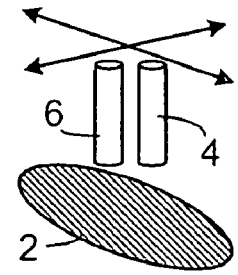
FIG. 1A
FIG. 1B
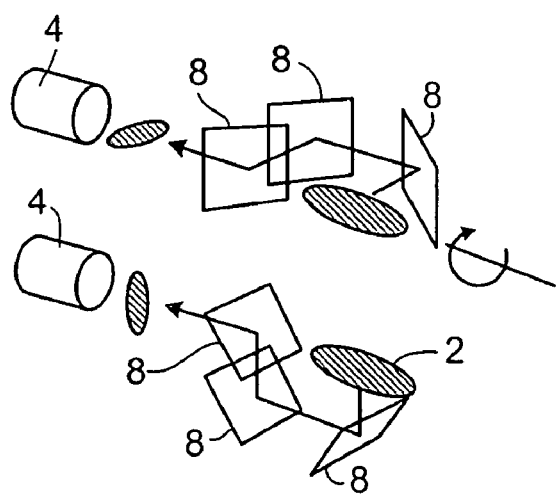
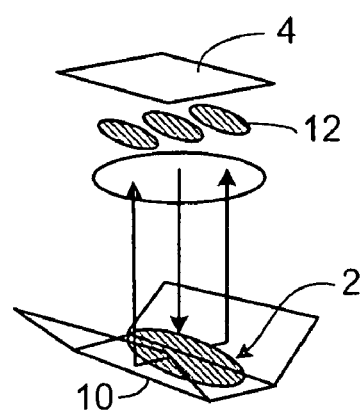
FIG. 1C
FIG. 1D

SYSTEMS AND METHODS FOR IN-VIVO AND OPTICAL IMAGING AND MEASUREMENT

CROSS-REFERENCE TO RELATED APPLICATIONS

This application claims priority to: U.S. Provisional Application No. 60/633,511 entitled "METHOD AND SYSTEM FOR CAPTURING MULTIPLE VIEWS OF AN EXTENDED, LUMINESCING SPECIMEN" by Clifford C. Hoyt and Peter Domenicali, filed on Dec. 6, 2004; U.S. Provisional Application No. 60/702,925 entitled "METHOD AND SYSTEM FOR CAPTURING MULTIPLE VIEWS OF AN EXTENDED, LUMINESCING SPECIMEN AND SEQUENTIAL ILLUMINATION THEREOF" by Clifford C. Hoyt and Peter Domenicali, filed on Jul. 27, 2005; U.S. Provisional Application No. 60/707,497 entitled "METHOD AND SYSTEM FOR CAPTURING MULTIPLE VIEWS OF AN EXTENDED, LUMINESCING SPECIMEN AND SEQUENTIAL ILLUMINATION THEREOF" by Clifford C. Hoyt and Peter Domenicali, filed on Aug. 11, 2005; U.S. Provisional Application No. 60/634,154 entitled "METHOD FOR DETERMINING THE DEPTH OF FLUORESCENCE ENTITIES INSIDE OBJECTS OR ORGANISMS" by Clifford C. Hoyt and James Mansfield, filed on Dec. 8, 2004; U.S. Provisional Application No. 60/720,080 entitled "METHOD AND SYSTEM FOR DETERMINING THE DEPTH OF FLUORESCENCE ENTITIES INSIDE OBJECTS OR ORGANISMS" by Clifford C. Hoyt and Peter Domenicali, filed on Sep. 23, 2005; and U.S. Provisional Application No. 60/697,617 entitled "METHOD AND SYSTEM FOR ESTIMATING BIOMASS TUMORS USING OPTICAL IMAGING" by Clifford C. Hoyt, filed on Jul. 8, 2005. The contents of each of the foregoing provisional applications are incorporated herein by reference.

TECHNICAL FIELD

This invention relates to optical imaging and in particular, to optical imaging in biological specimens.

BACKGROUND

Small animal optical imaging is an increasingly popular technique for studying tumors and other physiological conditions in-vivo in life sciences research and pharmaceutical drug development. Optical imaging techniques can provide low cost, rapid, and quantitative measurements compared to more conventional medical imaging techniques such as MRI, CAT, PET, and SPECT.

Optical imaging techniques typically capture images of a specimen using light in the ultraviolet, visible, and near-infrared (near-IR) regions of the electromagnetic spectrum. It can be difficult, however, to acquire accurate three-dimensional information via optical imaging when tissue, which is a turbid medium, is highly scattering and/or absorbs light at these wavelengths. Some imaging techniques detect spatial distributions of scattered, emitted and transmitted photons (or combinations thereof) emanating from a specimen. Further information about the internal structure of the specimen can be obtained from time-of-flight emission measurements, fluorescence lifetimes, and/or the spectral properties of emitted, scattered, and transmitted photons. In general, many different approaches are known and used for the detection of these photons.

Information about the distribution of light emanating from a specimen can be used as an input to a light diffusion algorithm in order to construct a 3D model of in-vivo entities based on the spatial light distribution, see for example U.S. patent application Ser. No. 10/606,976 entitled "METHOD AND APPARATUS FOR 3-D IMAGING OF INTERNAL LIGHT SOURCES" by Daniel G. Stearns et al., filed on Jun. 25, 2003, the contents of which are incorporated herein by reference. The accuracy of light diffusion algorithms, in general, is enhanced by light distribution information acquired from multiple views of the specimen. In consequence, measurement systems that provide multiple-view capability may be more sensitive and provide higher accuracy than single-view systems.

Systems that capture multiple views of a specimen can do so in various ways. Four techniques for recording multiple views of a specimen are shown in FIGS. 1A-D. FIG. 1A is a schematic diagram of an imaging system where multiple CCD cameras 4 are oriented about a specimen 2 in order to acquire multiple views of the specimen. FIG. 1B is a schematic diagram of a measurement system having a source 6 and a detector 4. Both source 6 and detector 4 are scanned over the surface of specimen 2 in order to capture multiple views of the specimen's surface. The arrows in the figure illustrate the scan directions. FIG. 1C is a schematic diagram of a measurement system that uses multiple mirrors 8 to direct two different views of specimen 2 to two detectors 4. FIG. 1D is a schematic diagram of a measurement system that employs a compound mirror 10 to direct two different side views of specimen 2 to an imaging lens 12, which images these views, along with a front view of specimen 2, to detector array 4.

Three-dimensional information about structures and entities inside living organisms is useful in both research and clinical applications. For example, in pharmaceutical pre-clinical trials, tumors can be grown in immuno-compromised animal models and tracked using imaging techniques such as fluorescence imaging. In some cases, image contrast can be enhanced by labeling entities with molecular fluorophores. The use of labels may also provide information about the internal structure of a specimen, such as the dimensions and/or density of particular internal features that have specific molecular characteristics. Detection of fluorescence emitted by a specimen is a preferred technique because the biochemistry of target-specific fluorescence labeling is well developed.

The advent of genetically engineered cell lines that express fluorescent proteins for in-vivo measurements provides a means to characterize an entity using a unique optical emission signal. These techniques are described, for example, by M. Chalfie et al. in "Green Fluorescent Protein as a Marker for Gene Expression," *Science* 263: 802-805 (1994), the contents of which are incorporated herein by reference. Exogenous fluorophores can therefore be introduced into internal structures such as tumors to enable fluorescence imaging by inducing the tumors to express fluorescent proteins, providing for a natural localization of the fluorescence emission within a specimen. In some cases, fluorophores that bind to a tumor can also be injected into a specimen.

The accuracy and resolution of in-vivo imaging of fluorescent entities in living organisms can be limited by scattering and absorption in tissues. These processes attenuate the intensity of light passing through the tissue. The effects of tissue scattering and absorption have been studied extensively, see for example T. L. Troy and S. N. Thennadil, "Optical properties of human skin in the near infrared wavelength range of 1000 to 2200 nm," *Journal of Biomedical Optics* 6: 167-176 (2004), the contents of which are incorporated herein by reference. At wavelengths from the ultraviolet to the near-infrared, it has generally been found that as the wavelength of incident light increases, both scattering and absorption of the incident light by tissue decrease. As a result, the effective "penetration depth" of incident light in tissue varies with wavelength. In the range of wavelengths from about 400 nm to about 1100 nm, the greatest penetration depth occurs at about 800 nm.

Absorption and scattering properties of biological tissues have been found to be substantially similar among animals, and this finding has been used as a basis for numerous optical techniques for probing turbid media with light. Computational techniques for reconstructing 3D tissue models that take into account measured spatial, temporal, and/or spectral information from light emitted or scattered by specimen tissues are used to visualize the specimen's internal structure. Monte Carlo methods may be used to validate these structural models, see for example Q. Liu, C. Zhu and N. Ramanujam, "Experimenal validation of Monte Carlo modeling of fluorescence in tissues in the UV-visible spectrum," *Journal of Biomedical Optics* 8: 223-236 (2003).

Depth or position information regarding entities within a specimen can be provided by measuring wavelength shifts of light emitted from the specimen, because the magnitude of the wavelength shift varies as a function of the thickness of tissue between the emitting entity and a detector. In particular, if a specimen emits light in a portion of the spectrum where the scattering and/or absorption properties have a substantially monotonic increase or decrease as a function of tissue thickness, then the emission spectrum of a labeled entity will shift as a function of the entity's position within the specimen. The shift of the emission spectrum may be small, i.e., a few nanometers, for significant changes in tissue thickness, so measurement equipment used to detect spectral shifts should have sensitivity that is sufficient to detect small spectral changes in order to make precise thickness estimates. Further, shifts of the emission spectrum can be produced via other mechanisms such as biochemical processes.

SUMMARY

We disclose systems and methods for extracting information about objects in dense or turbid media, e.g., tumors in biological specimens such as mice. In general, the systems include a light source and an imaging apparatus for capturing one or more views of the specimen under study. In many embodiments, the light source can be configured to cause the specimen or a structural entity therein to fluoresce, and the imaging apparatus captures one or more fluorescence images on a detector system.

In general, the systems are capable of operating in multiple measurement modes in order to record different types of information, thereby effecting various types of measurements. For example, the systems are capable of operating in an alignment or positioning mode, in which the position and orientation of a specimen are optimized prior to recording data based on a previously recorded reference image of the specimen. In addition, the systems can operate in a structured illumination mode. For example, one or more selected sides of a specimen can be illuminated sequentially, and one or more spatial intensity patterns can be imparted to the illumination light incident on any selected side of the specimen. Emitted light from the specimen can be detected in a single view of the specimen, or multiple views can be measured, simultaneously or in a selected sequential pattern. In some embodiments, the systems can be configured to measure a spectral response from the specimen by providing excitation light at multiple wavelengths and/or by resolving emission into various emission wavelengths. To improve the accuracy of data obtained from spectrally resolved measurements, multiple different fluorescence labels can be attached to entities of interest. Single- or multiple-view images that include spectral information can be used to provide position information about fluorescing entities internal to the specimen. In another mode of operation, the systems can be configured to integrate the total emitted radiation from a specimen, captured in one or more views or directions, and to estimate a mass of a structural entity emitting the measured radiation.

In each of the modes of system operation, various mechanisms may produce the radiation captured in views or measurements of the specimen. Incident light can be reflected, scattered, or transmitted by the specimen. In addition, an important mechanism is fluorescence, wherein light incident on a specimen induces the specimen (or a structural entity therein) to fluoresce. In some embodiments, the wavelength of the fluorescence is different (i.e., red-shifted) from the wavelength of the incident light, providing a convenient means for separating the signals. Fluorescence can be produced by chemical moieties naturally present in the specimen, or the fluorescent moieties can be introduced through biological (e.g., molecular genetic) or chemical (e.g., injection of structurally-specific labels) techniques. Chemical moieties naturally present in the specimen can produce autofluorescence and it may be necessary, in some cases, to distinguish an autofluorescence signal from fluorescence emission by a labeled entity in order to obtain accurate measurements. In addition, some specimens may exhibit bioluminescence, and light sources may not be required in order to measure luminescence images.

We now generally summarize different aspects and features of the invention.

In general, in one aspect, a method is disclosed including using multiple reflective surfaces of an optical component to direct two or more (and in some preferred embodiments, three or more) side views of an extended specimen (such as a small animal, like a mouse) to a detector system. The relative orientation of the specimen meets one or more of the following conditions: i) a long axis of the extended specimen is oriented parallel to an optical axis connecting the optical component to the detector system; ii) each view of the specimen is imaged onto the detector system via the optical component and defines chief rays, and the specimen oriented with respect to the optical component so that the chief rays for the different views emerge from the specimen substantially perpendicular to a long axis of the specimen; iii) each view of the specimen is imaged onto the detector system via the optical component, and the specimen is oriented with respect to the optical component so that optical paths between the specimen and the detector system for different views are substantially equal; and iv) a long axis of the extended specimen is oriented nominally collinear with a symmetry axis of the optical component.

Embodiments of the method may include any of the following features.

Each reflective surface of the optical component is a mirror configured to direct one view of the sample to the detector system. For example, the optical component may include a pyramidal arrangement of the mirrors.

The detector system may includes a CCD camera.

The method may further include using one or more lenses to image the multiple views onto the detector system.

The multiple reflective surfaces may be curved to image the multiple views onto the detector system.

The method may further including using one or more lenses between the optical component and the detector system to image the views from the specimen to the detector system. Alternatively, or in addition, the reflective surfaces of the optical component may be curved to image each view from the specimen to the detector system.

In another, related aspect, a system is disclosed including: a specimen holder configured to support an extended specimen (for example, a small animal, like a mouse); a detector system; and an optical component including two or more reflective surfaces (or in some preferred embodiments, three or more reflective surfaces) each configured to direct a different side view of the extended specimen to the detector system. The orientation of the specimen holder is set according to one or more of the following conditions: i) the specimen holder is configured to orient a long axis of the extended specimen parallel to an optical axis connecting the optical component to the detector system; ii) the specimen holder is configured to orient the extended specimen with respect to the optical component so that so the optical paths between the specimen and the detector system for different views are substantially equal; iii) the specimen holder is configured to orient the extended specimen with respect to the optical component so that chief rays for the different views emerge from the specimen substantially perpendicular to a long axis of the specimen; and iv) the specimen holder is configured to orient the extended specimen with respect to the optical component so that a long axis of the specimen is oriented nominally collinear with a symmetry axis of the optical component.

Embodiments of the system may include features corresponding to any of the features described above in connection with the related method.

In general, in another aspect, a method is disclosed including: (i) sequentially illuminating different sides of a sample; and (ii) using multiple reflective surfaces of an optical component to direct multiple side views (for example, in some preferred embodiments, three or more side views) of the sample to a detector system in response to each sequential illumination.

Embodiments of the method may include any of the following features.

The sequential illumination of the different sides of the sample may be done via the multiple reflective surface of the optical component.

The reflective surfaces of the optical component may have a dichroic coating, and the sequential illumination of the sample may pass through the dichroic coating and the multiple side views are reflected by the coating.

Each illumination in the sequential illumination may use a different one of the reflective surfaces to illuminate the sample.

The sequential illumination may includes using a spatial light modulator to selectively direct light to the different sides of the sample.

The sequential illumination may includes using multiple fiber bundles as the light source. For example, each fiber bundle may be used to illuminate a corresponding one of the sides of the sample.

One or more dichroic beamsplitters may be used to guide light from the sample along a path different from that of light used to illuminate the sample.

The method may further include positioning the spatial light modulator in a plane conjugate to that of the detector system The method may further include positioning the spatial light modulator in a plane conjugate to that of the sample.

The method may further include adjusting the configuration of the spatial light modulator to improve the uniformity of the illumination at the sample The method may further including adjusting the configuration of the spatial light modulator to improve the uniformity of one or more of the side views as measured by the detector system.

The relative orientation of the specimen may be set to meet one or more of the following conditions: i) a long axis of the extended specimen is oriented parallel to an optical axis connecting the optical component to the detector system; ii) each view of the specimen is imaged onto the detector system via the optical component and defines chief rays, and the specimen oriented with respect to the optical component so that the chief rays for the different views emerge from the specimen substantially perpendicular to a long axis of the specimen; iii) each view of the specimen is imaged onto the detector system via the optical component, and the specimen is oriented with respect to the optical component so that optical paths between the specimen and the detector system for different views are substantially equal; and iv) a long axis of the extended specimen is oriented nominally collinear with a symmetry axis of the optical component.

Each reflective surface of the optical component may be a mirror configured to direct one view of the specimen to the detector system. The optical component may include a pyramidal arrangement of the mirrors. The detector system may include a CCD camera.

The method may further include using one or more lenses to image the multiple views onto the detector system.

The multiple reflective surfaces may be curved to image the multiple views onto the detector system.

In a related aspect, a system is disclosed that includes: (i) a specimen holder configured to support an extended specimen; (ii) a detector system; (iii) an optical component including multiple reflective surfaces each configured to direct a different side view of the extended specimen to the detector; and (iv) an illumination source configured to sequentially illuminate different sides of the specimen.

Embodiments of the system may include any of the following features.

The illumination source may be configured to sequentially illuminate the different sides of the specimen via the multiple reflective surfaces of the optical component.

The reflective surfaces of the optical component may have a dichroic coating, and the sequential illumination from the illumination source may pass through the dichroic coating and the side views are reflected by the coating.

The multiple reflective surfaces may include three of more reflective surfaces.

The orientation of the specimen holder may be set according to one or more of the following conditions: i) the specimen holder is configured to orient a long axis of the extended specimen parallel to an optical axis connecting the optical component to the detector system; ii) the specimen holder is configured to orient the extended specimen with respect to the optical component so that so the optical paths between the specimen and the detector system for different views are substantially equal; iii) the specimen holder is configured to orient the extended specimen with respect to the optical component so that chief rays for the different views emerge from the specimen substantially perpendicular to a long axis of the specimen; and iv) the specimen holder is configured to orient the extended specimen with respect to the optical component so that a long axis of the specimen is oriented nominally collinear with a symmetry axis of the optical component.

The system may include one or more lenses to image each view onto the detector system.

Each reflective surface of the optical component may be curved to image the corresponding view onto the detector system.

The illumination source may be configured so that each illumination in the sequential illumination uses a different one of the reflective surfaces to illuminate the sample.

The illumination source may includes multiple fiber bundles. For example, each fiber bundle may be used to illuminate a corresponding one of the sides of the specimen.

The system may further include one or more dichroic beam splitters to guide light from the specimen along a path different from that of light used to illuminate the specimen.

The illumination source may includes light conditioning optics including a spatial light modulator. The spatial light modulator may be positioned in a plane conjugate to that of the detector system or positioned in a plane conjugate to that of the specimen holder.

The system may further include an electronic controller coupled to the spatial light modulator and configured to adjust the configuration of the spatial light modulator to improve the uniformity of the illumination at the sample and/or to improve the uniformity of one or more of the side views measured by the detector system.

In general, in another aspect, a method is disclosed including: (i) sequentially illuminating a specimen with different spatial distributions of light, wherein each illumination causes an object embedded in the specimen to emit radiation in response to the light; (ii) for each different spatial distribution of illumination light, imaging the radiation emitted from the specimen from each of multiple sides of the specimen (for example, in preferred embodiments, from three or more sides of the specimen); and (iii) determining information about the object in the specimen based on the imaged radiation from each of the multiple sides for each of the different spatial distributions of illumination light.

Embodiments of the method may include any of the following features.

The emitted radiation may be fluorescence.

The different spatial distributions of illumination light may correspond to light distributions that illuminate different sides of the specimen. For example, each spatial distributions may have a common shape with respect to its side of the specimen, or it may have a different shape with respect to its side of the specimen.

At least some of the spatial distributions may correspond to different illumination patterns for a common side of the specimen.

The different illumination patterns may be produced by one or more of the following: (i) adjusting a position of an illumination light beam on the common side of the specimen; ii) using multiple fiber light sources; iii) using beam splitting optics to separate portions of light produced by a light source; and iv) using a spatial light modulator.

Imaging the radiation emitted from the specimen from each of multiple sides of the specimen may include one or more of the following: (i) using a multiple reflective surfaces of an optical component to collect emission from corresponding sides of the specimen; ii) using multiple detectors positioned to collect emission from the respective sides of the specimen; and (iii) using multiple optical fibers positioned to collect emission from the respective sides of the specimen.

The multiple sides may be separated from one another by more than 30 degrees. For example, they may be separated from one another by approximately 90 degrees.

The information about the object in the specimen may includes information about a relative position of the object within the specimen. For example, the information about the object in the specimen may further include information about an orientation and shape of the object in the specimen. Also, the information about the object in the specimen may include information about a size the object in the specimen.

The specimen may be an animal (for example, a small animal, such as a mouse). The animal may be living. The object in the specimen may be tumor in the animal.

Determining information about the object in the specimen may include constructing a self-consistent model of the object in the specimen based on imaged radiation from the multiple sides of the sample for each of the different spatial distributions of illumination light.

For each different spatial distributions of illumination light, the illumination of the sample may include illuminating with a common set of different excitation spectra, and the information about the object in the specimen is further based on the differences in the imaged radiation for each of the different excitation spectra for each of the different spatial distributions. In such cases, the method may further including removing autofluorescence from the imaged radiation.

In other embodiments, the method may further include spectrally resolving the radiation emitted from each side of the specimen, and wherein the information about the object in the specimen is further based on the differences in the variations in the spectral content of the imaged radiation.

In a related aspect, an apparatus is disclosed including: (i) a source configured to sequentially illuminate a specimen with different spatial distributions of light, wherein each illumination causes an object embedded in the specimen to emit radiation in response to the light; (ii) a detector system configured to image the radiation emitted from the specimen from each of multiple sides of the specimen for each of the different spatial distributions of illumination light; and (iii) an electronic processor coupled to the source and detector system, the processor configured to determine information about the object in the specimen based on the imaged radiation from each of the multiple sides for each of the different spatial distributions of illumination light. The source may include light conditioning optics for producing the different spatial distributions of light. The detector system include may include light collection optics for imaging the emitted radiation to one or more detectors.

Embodiments of the apparatus may include features corresponding to any of the features listed above in connection with the related method.

In general, in another aspect, a method is disclosed including: (i) illuminating a living specimen to cause an object embedded in the specimen (e.g., a living animal) to emit radiation in response to the illumination, wherein the specimen has eyes and the illumination extends over a region of the specimen including the eyes; (ii) shaping the illumination to prevent it from exposing the eyes of the specimen; and (iii) measuring the emitted radiation to determine information about the object embedded in the specimen.

Embodiments of the method may include any of the following features.

For example, the shaping may include positioning an optical element between the source of the illumination and the eyes of the specimen and/or using a spatial light modulator to prevent the illumination from exposing the eyes of the specimen.

The shaping may prevent involuntary movement of the specimen caused by illuminating the eyes.

The emitted radiation may be imaged to a detector from each of multiple sides of the specimen.

In a related aspect, an apparatus is disclosed including: (i) a source configured to illuminate a living specimen to cause an object embedded in the specimen to emit radiation in response to the illumination, wherein the specimen has eyes and wherein the illumination extends over a region of the specimen including the eyes; (ii) a means for shaping the illumination to prevent it from exposing the eyes of the specimen; (iii) a detector system for measuring the emitted radiation; and (iv) an electronic process coupled to the detector system and configured to determine information about the object embedded in the specimen.

Embodiments of the apparatus may include any of the following features.

The means for shaping may be an optical element positioned between the source of the illumination and the eyes of the specimen. For example, the optical element may be a stop or mirror. The optical element may be configured to be adjustably positioned.

In another aspect, a method is disclosed including providing a sample having an entity embedded therein that is labeled with multiple fluorescence compounds having different emission spectra, illuminating the sample to cause emission from the labeled entity, measuring an intensity of the emission at each of multiple emission wavelengths, and determining information about a position of the entity within the sample based on the measured emission at each of the different emission wavelengths.

Embodiments of the method may include any of the following features.

The sample may be a biological sample, such as a living animal.

The entity may be a tumor.

The emission may be measured at each of three or more different emission wavelengths, or at each of four or more different emission wavelengths.

The information about the position of the entity within the sample may be determined based further on information about the relative absorption of the different emission wavelengths in the sample and the relative emission intensity of the entity at each of the different emission wavelengths.

The position information may be determined to account for scaling of the relative emission intensity of the entity at each of the different emission wavelengths caused by differential absorption of the emission wavelengths in the sample when the emission propagates through the sample.

The multiple fluorescent compounds labeling the entity may produce emission peaks over a range larger than 60 nm. The multiple fluorescent compounds labeling the entity may produce emission peaks over a range larger than 100 nm.

The multiple fluorescent compounds labeling the entity may produce emission peaks large enough to produce a differential attenuation between at least two of the emission peaks that is larger than two times (e.g., larger than five, or even ten times) for every centimeter of depth in the sample material surrounding the entity.

The position information may be determined based further on calibration data for the emission spectra of the fluorescent compounds labeling the entity.

The intensity of the emission at each of multiple emission wavelengths may be measured from each of multiple sides of the sample, and the position information may be based on the measured emission at each of the different emission wavelengths from each of the multiple sides of the sample.

In a related aspect, a system is disclosed including: (i) a light source system configured to illuminate a sample, where the sample has an entity embedded therein that is labeled with multiple fluorescence compounds having different emission spectra and wherein the illumination of the sample causes emission from the labeled entity; (ii) a detector system configured to measure an intensity of the emission at each of multiple emission wavelengths; and (iii) an electronic processor coupled to the detector system, where the electronic processor is configured to determine information about a position of the entity within the sample based on the measured emission at each of the different emission wavelengths and calibration data about the different emission spectra of the fluorescence compounds labeling the entity embedded in the sample.

Embodiments of the system may have any of the following features.

The electronic processor may be configured to determine information about a position of the entity within the sample based further on calibration data about the differential absorption of material in the sample surrounding the embedded entity for the different emission wavelengths.

Embodiments of the system may further include features corresponding to any of the features listed above in connection with the related method.

In general, in another aspect, the invention a method is disclosed that includes illuminating a sample at each of at least two different excitation wavelengths, measuring radiation emitted from an entity embedded in the sample in response to each of the excitation wavelengths, and determining information about the position of the entity in the sample based on the measured radiation corresponding to the illumination at each of the different excitation wavelengths.

Embodiments of the method may include any of the following features.

The sample may be a biological sample, such as a living animal.

The entity may be a tumor labeled with a fluorescent material.

The radiation may be directed to the sample at each of three or more different excitation wavelengths, and the radiation emitted from the entity may be measured in response to each of the three or more different excitation wavelengths.

For each excitation wavelength for which the radiation emitted from the entity is measured, the relative intensity of emitted radiation at two or more emission wavelengths may be measured. The measured relative intensities of the emitted radiation at the two or more emission wavelengths may be used to reduce the contribution of autofluorescence from the measured radiation used to determine the entity depth. The reduction of the contribution of autofluorescence may be based on a linear decomposition of the measured relative intensities in terms of spectral signatures for the entity and one or more other components of the sample. For example, for each excitation wavelength for which the radiation emitted from the entity is measured, the relative intensity of emitted radiation at two or more emission wavelengths may be measured. The measured relative intensities of the emitted radiation at the two or more emission wavelengths may be used to reduce the contribution of autofluorescence from the measured radiation used to determine the entity depth, and the reduction of the contribution of autofluorescence may be based on a linear decomposition of the measured relative intensities in terms of spectral signatures for the entity and one or more other components of the sample.

The position information may be determined based further on information about the relative absorption of the different excitation wavelengths in the sample and the relative emission intensity of the entity at each of the different excitation wavelengths. The position information may be determined based further to account for scaling of the relative emission intensity of the entity at each of the different excitation wavelengths caused by differential absorption of the excitation wavelengths caused by material in the sample through which the excitation wavelengths pass to be incident on the entity.

The excitation wavelengths may be in a range of about 540 nm to about 650 nm, and the emitted radiation may be in a range of about 750 nm to about 900 nm.

The sample may be sequentially illuminated on each of multiple sides of the sample, and the emitted radiation may be measured in response to each of the excitation wavelengths for the illumination of each of the sides, and the position information may be determined based on the radiation measured by the detector system at each of the different excitation wavelengths for the illumination of each of the sides.

In a related aspect, a system is disclosed including a light source system configured to illuminate a sample at each of at least two different excitation wavelengths, a detector system configured to measure radiation emitted from an entity embedded in the sample in response to each of the excitation wavelengths, and an electronic processor configured to determine information about the position of the entity within the sample based on the radiation measured by the detector system corresponding to the illumination at each of the different excitation wavelengths.

Embodiments of the system may further include features corresponding to any of the features listed above in connection with the related method.

In general, in another aspect, a method is disclosed that includes collecting radiation emitted from an object embedded in a biological sample from multiple sides of the sample, and estimating the size of the object based on the collected radiation.

Embodiments of the method may include any of the following features.

Collecting the radiation may include collecting radiation emitted from the object through substantially all surfaces of the sample.

The collected radiation may only be a fraction of the total flux of radiation emitted from the object through substantially all surfaces of the sample. The collected radiation may be used to determine an index for the total flux, and the size of the object may be estimated based on the index and calibration information that correlates the index to the object size. Further, the index may be determined by integrating the radiation collected from the multiple sides of the object.

The object may be spaced from all of the surfaces of the sample by more than a millimeter.

The emitted radiation may be fluorescence or bioluminescence.

The object may be a tumor and the sample may be an animal.

The object may be labeled with a compound that causes the emitted radiation to be in a selected range of wavelengths. For example, the emitted radiation may be in the near-infrared region of the spectrum, such as from about 700 nm to about 900 nm.

Estimating the size of the object may include integrating the emitted radiation and estimating the size of the object based on the integrated radiation. Estimating the size of the object may further include estimating the mass of the object from the integrated radiation and estimating the size of the object based on the estimated mass of the object. Further, estimating the size of the object may include determining spatially resolved information about the sample from at least some of the collected information and using the spatially resolved information to improve the estimation of the size of the object.

Collecting the emitted radiation may include using spectral unmixing techniques to remove autofluorescence from the sample. For example, using spectral unmixing techniques may include measuring the relative intensity of the collected radiation at two or more emission wavelengths, using the measured relative intensities of the collected radiation at the two or more emission wavelengths to adjust them to account for autofluorescence, and using the adjusted intensities to estimate the size of the embedded entity. The two or more emission wavelengths may include, for example, three or more emission wavelengths, or four or more emission wavelengths. Accounting for the autofluorescence, for example, may be based on a linear decomposition of the measured intensities in terms of spectral signatures for the object and one or more other components of the sample.

Illumination of the sample may be used to induce the emission of the radiation from the object.

Collecting the radiation emitted from the object from the multiple sides of the sample may include imaging the radiation emitted through each side of the object to a detector system. An optical element having multiple reflective surfaces may be used to image the multiple sides of the sample to the detector system.

In a related aspect, a system is disclosed including optics for collecting radiation emitting from an object embedded in a biological sample from multiple sides of the sample, a detector system for receiving the radiation collected by the optics, and an electronic processor coupled to the detector for estimating the size of the object based on the collected radiation.

Embodiments of the system may include any of the following features.

The collecting optics may be configured to collect radiation emitted from the object through substantially all surfaces of the sample.

The collecting optics may be configured to collect only a fraction of the total flux of radiation emitted from the object through substantially all surfaces of the sample. Further, an electronic processor may be configured to use the collected radiation to determine an index for the total flux and estimate the size of the object based on the index and calibration information that correlates the index to the object size. For example, the electronic processor may be configured to determine the index based on the integrated radiation collected from the multiple sizes of the object.

A mount may be used to secure the biological sample relative to the optics.

The system may include an illumination source.

The collecting optics may include a pyramidal arrangement of mirrors and an imaging lens.

The detector system may be a multi-element detector.

The detector system may include multiple detectors corresponding to different sides of the sample.

The detector system may be configured to measure the relative intensity of the collected radiation at two or more emission wavelengths, and the processor may be configured to adjust the measured relative intensities of the collected radiation at the two or more emission wavelengths to adjust for autofluorescence from the sample and use the adjusted intensities to estimate the size of the embedded entity. The two or more emission wavelengths may include, for example, three or more emission wavelengths, or four or more emission wavelengths. For example, the processor may be configured to adjust for the autofluorescence based on a linear decomposition of the measured intensities in terms of spectral signatures for the object and one or more other components of the sample that produce the autofluorescence.

In general, in another aspect, a method is disclosed that includes positioning a specimen inside an optical measurement system according to a reference image of the specimen indicative of its position and orientation during an earlier measurement using the optical measurement system, and measuring radiation emitted from the positioned specimen to provide information about an object embedded in the specimen.

Embodiments of the method may include any of the following features.

The reference image may be recorded more than one hour (e.g., more than one day) prior to the present positioning of the specimen.

The reference image may be recorded based on a light reflected or scattered from the specimen, or based on a fluorescent light emitted from the specimen.

The emitted radiation may be fluorescence or bioluminescence.

The positioned specimen may be illuminated to cause the emitted radiation.

The emitted radiation may include radiation emitted from the object embedded in the specimen.

The specimen may be a living animal, and the object may be a tumor embedded in the animal.

Information about the object may be compared to information derived from the earlier measurement of the specimen.

At a later time, the specimen may be positioned inside the optical measurement system according to the reference image for a subsequent measurement using the optical measurement system to provide information about the object embedded in the specimen at a later time.

The information about the object may include information about the size, position, or shape of the object.

The earlier measurement may be performed and the reference image may be recorded.

The specimen may be positioned to match the position and orientation of the reference image.

A live image of the specimen may be obtained while positioning the specimen, and the specimen may be positioned based on a comparison between the live image and the reference image. The live image may be processed to highlight edges or other features of the specimen to aid in the positioning. The live image and the reference image may be simultaneously displayed to aid in the positioning of the specimen. The live image and the reference image may further be superimposed to aid in the positioning of the specimen. The comparison may include providing a numerical index, based on image processing techniques, to indicate the degree to which the same orientation is achieved in live and reference images. A display element may be provided, which changes in accordance with the value of the numerical index. Determining whether to measure the emitted radiation may be based on the value of the numerical index, and the determination may be made automatically by the optical measurement system. For example, the optical measurement system may illuminate the sample to cause the emitted radiation when it determines that the value of the numerical index indicates a sufficient match between the live image and the reference image.

The reference image may be processed to highlight edges or other features to aid in the repositioning.

The reference image may be adjusted to account for changes in the size or shape of the specimen since the earlier measurement by the optical measurement system.

In a related aspect, a system is disclosed that includes an optical measurement system configured to measure radiation emitted from a specimen, where the optical measurement system includes an adjustable stage for positioning the specimen and an electronic processor configured to determine information about an object embedded in the specimen based on the measured radiation emitted from the specimen, and where the electronic processor further stores a reference image of the specimen indicative of its position and orientation during an earlier measurement using the optical measurement system.

Embodiments of the system may include any of the following features.

The reference image may be recorded based on a light reflected or scattered from the specimen, or based on a fluorescent light emitted from the specimen.

The optical measurement system may be configured to illuminate the specimen to cause the emitted radiation. The emitted radiation may include radiation emitted from the object embedded in the sample.

The processor may be configured to compare the determined information about the object to information derived from the earlier measurement of the specimen.

The information about the object may include information about the size, position, or shape of the object.

The optical measurement system may be configured to perform the earlier measurement and record the reference image.

The optical measurement system may be configured to obtain a live image of the specimen while positioning the specimen on the stage. The optical measurement system may further include a display coupled to the electronic processor and configured to simultaneously display the live image and the reference image to aid in the positioning of the specimen. The processor may be configured to process the live image to highlight edges or other features of the specimen to aid in the positioning, and the processor may be configured to compare the live image to the reference image and produce a numerical index, based on image processing techniques, to indicate the degree to which the same orientation is achieved in live and reference images. Further, the optical measurement system may include a display coupled to the electronic processor for providing a display indication which changes in accordance with the value of the numerical index. The electronic processor may be configured to determine whether to measure the emitted radiation based on the value of the numerical index. The optical measurement system may be configured to illuminate the specimen to cause the emitted radiation when it determines that the value of the numerical index indicates a sufficient match between the live image and the reference image.

The processor may be configured to process the reference image to highlight edges or other features to aid in the repositioning.

The electronic processor may be configured to adjust the reference image to account for changes in the size or shape of the specimen since the earlier measurement by the optical measurement system.

Unless otherwise defined, all technical and scientific terms used herein have the same meaning as commonly understood by one of ordinary skill in the art to which this invention belongs. In case of conflict with documents incorporated herein by reference, the present specification will control.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a schematic diagram of several different techniques for acquiring multiple views of a specimen.

Like reference symbols in the various drawings indicate like elements.

DETAILED DESCRIPTION OF PREFERRED EMBODIMENTS

Figure 2:
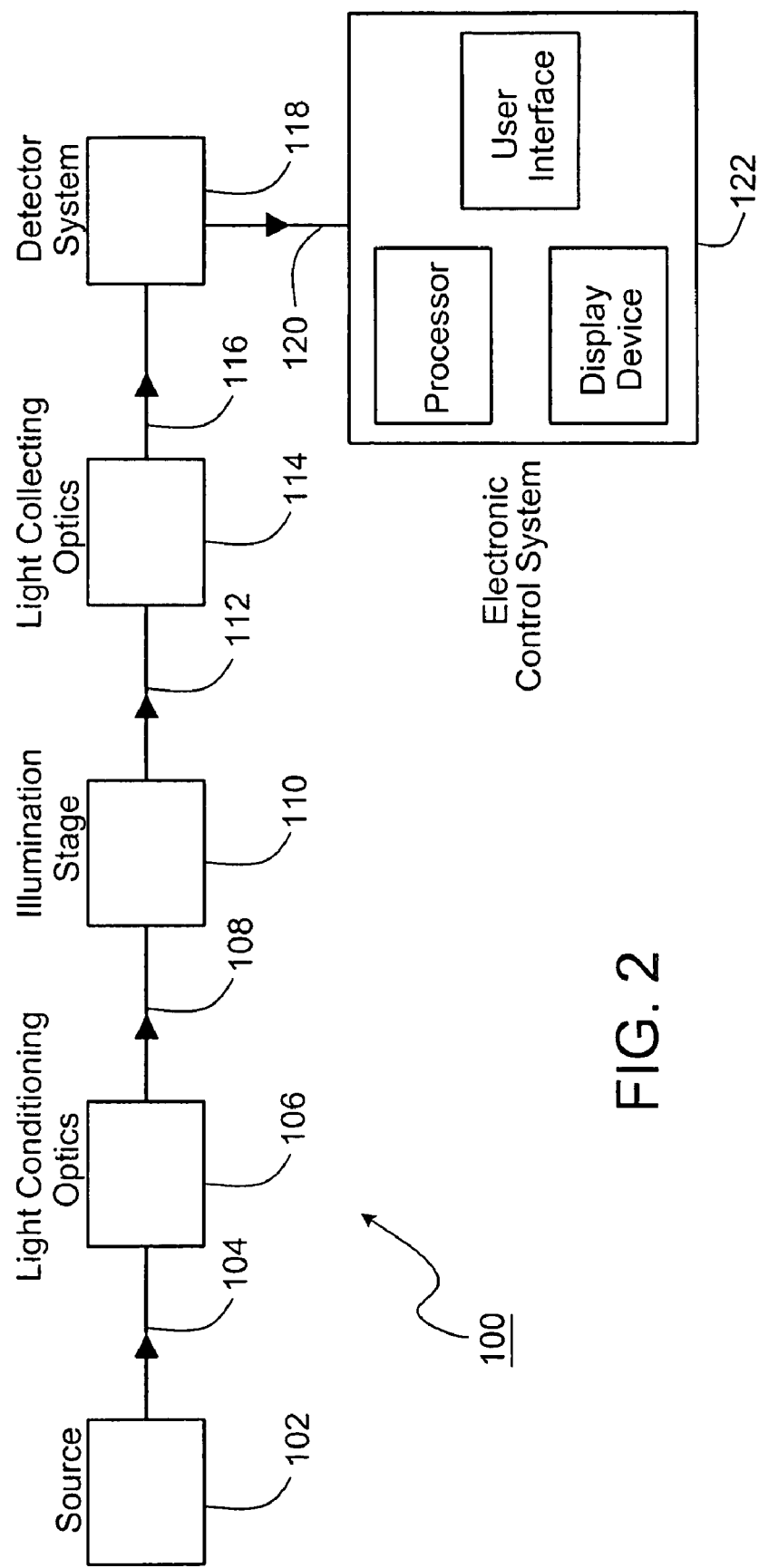
FIG. 2 is a schematic diagram of a measurement system for in-vivo biological imaging and measurement applications.

We disclose systems and methods for extracting information about objects in dense or turbid media, e.g., tumors in biological specimens such as mice. In general, the systems include a light source and an imaging apparatus for capturing one or more views of the specimen under study. In many embodiments, the light source can be configured to cause the specimen or a structural entity therein to fluoresce, and the imaging apparatus captures one or more fluorescence images on a detector system.

In general, the systems are capable of operating in multiple measurement modes in order to record different types of information, thereby effecting various types of measurements. For example, the systems are capable of operating in an alignment or positioning mode, in which the position and orientation of a specimen are optimized prior to recording data based on a previously recorded reference image of the specimen. In addition, the systems can operate in a structured illumination mode. For example, one or more selected sides of a specimen can be illuminated sequentially, and one or more spatial intensity patterns can be imparted to the illumination light incident on any selected side of the specimen. Emitted light from the specimen can be detected in a single view of the specimen, or multiple views can be measured, simultaneously or in a selected sequential pattern. In some embodiments, the systems can be configured to measure a spectral response from the specimen by providing excitation light at multiple wavelengths and/or by resolving emission into various emission wavelengths. To improve the accuracy of data obtained from spectrally resolved measurements, multiple different fluorescence labels can be attached to entities of interest. Single- or multiple-view images that include spectral information can be used to provide position information about fluorescing entities internal to the specimen. In another mode of operation, the systems can be configured to integrate the total emitted radiation from a specimen, captured in one or more views or directions, and to estimate a mass of a structural entity emitting the measured radiation.

In each of the modes of system operation, various mechanisms may produce the radiation captured in views or measurements of the specimen. Incident light can be reflected, scattered, or transmitted by the specimen. In addition, an important mechanism is fluorescence, wherein light incident on a specimen induces the specimen (or a structural entity therein) to fluoresce. In some embodiments, the wavelength of the fluorescence is different (i.e., red-shifted) from the wavelength of the incident light, providing a convenient means for separating the signals. Fluorescence can be produced by chemical moieties naturally present in the specimen, or the fluorescent moieties can be introduced through biological (e.g., molecular genetic) or chemical (e.g., injection of structurally-specific labels) techniques. Chemical moieties naturally present in the specimen can produce autofluorescence and it may be necessary, in some cases, to distinguish an autofluorescence signal from fluorescence emission by a labeled entity in order to obtain accurate measurements. In addition, some specimens may exhibit bioluminescence, and light sources may not be required in order to measure luminescence images.

Measurement Systems

A system 100 for capturing one or more views of a specimen is shown schematically in FIG. 2. The system includes a light source 102, light conditioning optics 106, an illumination stage 110, light collecting optics 114, a detector system 118, and an electronic control system 122. Light source 102 provides light 104 which is directed into light conditioning optics 106. Light conditioning optics 106 can include, for example, one or more optical elements configured to direct light towards illumination stage 110. In addition, light conditioning optics 106 can include optical elements configured to modulate one or more properties of light 104, such as the spectral properties or the spatial intensity distribution of light 104. The action of light conditioning optics 106 on light 104 produces illumination light 108, which is further directed by light conditioning optics 106 to be incident on a specimen (not shown) that is mounted on illumination stage 110.

Illumination light 108 can interact with the specimen in various ways to produce emitted light 112. For example, illumination light 108 can be scattered from the specimen, reflected by the specimen, transmitted by the specimen, or absorbed by the specimen. In many embodiments, light absorbed by the specimen may cause the specimen to fluoresce, producing additional light that can be included in emitted light 112. Further, some specimens may include bioluminescent structural entities therein, which emit light even in the absence of the action of illumination light 108.

Emitted light 112, which can include light produced by any of the foregoing mechanisms, is collected by light collecting optics 114. Light collecting optics 114 can be configured, for example, to capture one or more views of the specimen, the views corresponding to images of the specimen taken from different spatial observation points and providing different perspective views of the specimen. The views 116 of the specimen are directed by light collecting optics 114 to be incident on a detector system 118 configured to record each of the one or more views and to convert each to an electronic signal 120. An electronic control system 122 coupled to the detector system receives the electronic signals 120 and provides for further processing and system control.

Positioning Mode

Time-series measurements of structures or entities within a specimen can provide valuable information to researchers and clinicians. For example, time-series measurements of tumor size can be used to determine the rate of tumor growth and, in some applications, the effectiveness of pharmaceutical agents employed to counteract tumor growth. Successive measurements of the same specimen, however, can be separated by periods of hours, days, weeks, or months. Therefore, these time-series measurements can be susceptible to variance that appears due to measurement error introduced by non-reproducible positioning and orientation of a specimen with respect to the measurement apparatus. If the variability of the measured data over time is too large, for example, the value of the data for research purposes can be reduced.

In a first measurement mode, the system shown schematically in FIG. 2 can be operated in a positioning mode in order to reproducibly position and orient a specimen prior to beginning a measurement in order to reduce errors due to non-repeatable positioning and/or orientation in time-series measurements. In particular, variable placement of the specimen over a sequence of measurements can result in spurious errors due to spatial variation in illumination intensity, from simple shadowing caused by the specimen's shape, and from changes in specimen posture which rearranges internal structures and overlying tissues. In order to produce high quality data, reproducing the posture and position of the specimen from one measurement to the next (within a reasonable tolerance) can be an important consideration. The measurement systems disclosed above therefore provide for operation in a positioning mode.

Figure 3:
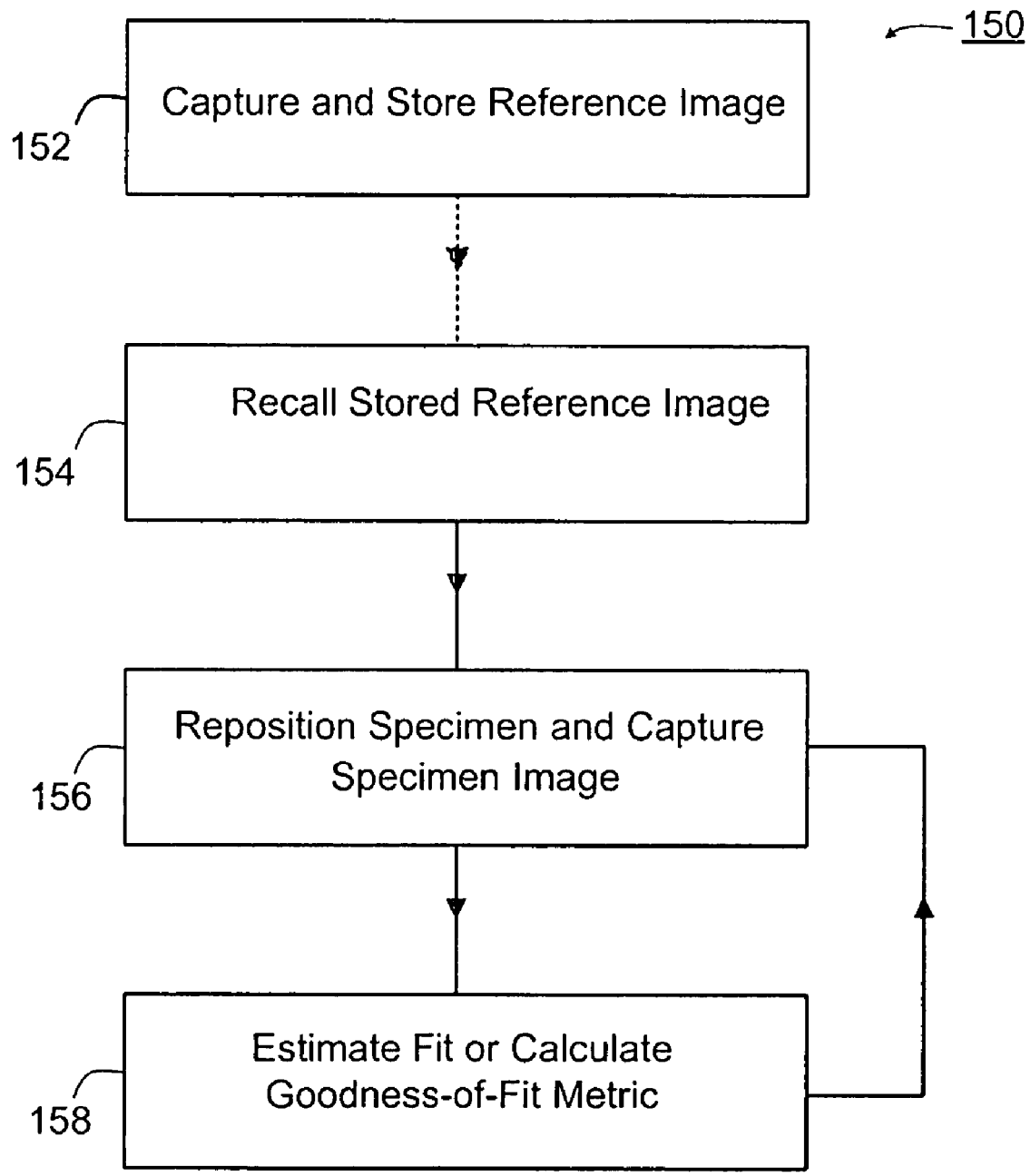
FIG. 3 is a flow chart that includes steps for reproducibly positioning a specimen prior to making measurements with the system of FIG. 2.

FIG. 3 is a flow chart 150 showing the steps involved in operating the system in a positioning mode. The first step 152 is to capture and store a reference image of the specimen. This step can be performed in conjunction with a fluorescence measurement, i.e., before or after a first fluorescence measurement in a time-series of measurements. The reference image can be taken with white light or another broadband source, or with a narrowband source. The reference image can, in general, be captured in any imaging modality, such that it records the orientation and position of the specimen in sufficient detail so that the recorded information can be used prior to future measurements in order to re-position the specimen. The reference image functions as a guide regarding the positioning and orientation of the specimen for future measurement sessions.

In general, the captured reference image can be a grayscale or color image. The reference image can be further processed using image processing techniques to highlight edges and/or significant anatomical features to aid the operator in the future positioning of the specimen.

The second step 154 of flow chart 150 is performed when a subsequent measurement session with the specimen is initiated. The reference image is recalled and used as a guide for specimen positioning. For example, the reference image can be projected onto a display device that is part of electronic control system 122 while the operator arranges the specimen. A live view of the specimen can be shown beside or superimposed upon the reference image. In some embodiments, the reference and live images may be displayed in different colors, so that when the images are superimposed, a third color is produced, highlighting the portions of the two images which do not overlap. For example, the reference image can be shown in red and the live image in green. When the two images are superimposed, the portions where the reference and live images overlap appear in a color that is the additive sum of the colors of the two separate images.

Further, when measurement system 100 is configured to capture multiple views of the specimen, both the reference and the live images can display the multiple views, providing extra information for the operator to aid in positioning the specimen.

The third step 156 in flow chart 150 involves positioning and orienting the specimen in order to match the reference image. It may not be possible to exactly match the current specimen position and/or orientation with the reference image for various reasons. For example, the specimen may have grown in size during the intervening time period. Therefore, the operator may decide upon a matching tolerance within which specimen placement is deemed acceptable.

This decision can be aided in the fourth step 158 of the procedure by estimation or computation of a positioning quality metric by electronic control system 122. The computational step is not necessary and may be omitted in some embodiments, such as when an operator judges goodness-of-fit visually based on a display. When employed, electronic control system 122 may, for example, use the reference and live images to compute a goodness-of-fit metric to quantify the degree of alignment between the two images and the accuracy of the positioning. The computed accuracy metric can be displayed to the operator using a color indicator, a numerical readout, a bar indicator, or the like. A suitable goodness-of-fit metric can be as simple as a normalized correlation measure for the live image and the reference image, for example. Alternatively, or in addition, a biometric approach may be taken, wherein points of reference such as the toes, eyes, ears, and skin folds are identified and their locations compared, where the goodness-of-fit metric is a mathematical function of the displacement of one or more selected reference points between the two images.

Step 158 may further incorporate a threshold condition indicating whether specimen positioning is sufficient for recording new measurements. For example, electronic control system 122, based on the results of a computed goodness-of-fit metric, can be configured to prevent further measurements from occurring until the specimen is sufficiently well-positioned. This feature can be used to ensure the integrity of measured data.

In response to a computed quality metric, or simply to visual interpretation of matching between the reference and live images, repositioning of the specimen by the operator may be required. In general, steps 156 and 158 illustrated in flow chart 150 can continue in cyclic fashion until the computed metric is satisfied or the operator determines that the alignment of the specimen is sufficiently precise.

In general, it is advantageous to record both reference and live images of the specimen using the same imaging optical elements (i.e., lenses, filters, detectors) in order to ensure that optical system parameters do not change between measurements. In the event that optical system parameters do change, however, or in the event that the specimen size or shape changes over time, the reference image may be warped using image processing techniques in order to produce a reference image that more closely matches the present condition of the imaging system and the specimen.

It may also be advantageous in some embodiments to use structured light to record the reference and live images of the specimen. As discussed further below, the use of structured light, where the spatial intensity profile of the illumination source varies, may provide additional information that can be used in order to ensure a more optimum orientation and position of the specimen. For example, structured light can be used to produce a light "grid" overlaying the surface of a specimen in a reference image. In subsequent re-positioning steps, the same grid can be reproduced using structured light and the specimen arranged such that the overlay of the grid on its surface matches the grid overlay in the reference image.

In some embodiments, positioning and orientation of the specimen is performed in a low-light environment. For example, detector system 118 can be configured, in other operating modes, to capture low intensity measurement signals such as fluorescence signals. In order to prevent stray light from damaging detector system optics, portions of measurement system 100 (or the entire system) may be enclosed within a light-tight box. The light source used for positioning can be chosen to be a light source that is also used to induce fluorescence emission from the labeled specimen. In the current operating mode, the light source provides radiation at a wavelength that passes through an emission barrier filter. Alternatively, in some embodiments, the emission barrier filter can be replaced by a standard fluorescence emission filter. In general, light source 102 provides radiation at a particular wavelength for operation in positioning mode so that detection system 118 measures a signal that arises from direct reflection or transmission of illumination light, rather than fluorescence emission by the specimen. Operation in positioning mode can further entail a reconfiguration of light conditioning optics 106 and/or light collecting optics 114 in order to provide for detection of appropriate images by detector system 118. For example, filters and other elements for manipulating the wavelength spectrum of light can be repositioned in order to create a suitable spectral configuration for illumination light 108.

In positioning mode, light source 102 can be a broadband light source, i.e., a white light source, or light source 102 can have a narrower bandwidth. Light source 102 can be a multi-wavelength source, for example, where one of the wavelengths is used when the system operates in positioning mode, and one or more other wavelengths are used in other modes of operation. Similarly, detection system 118 can include a single detector for multiple modes of operation, including positioning mode, or detection system 118 can include one or more detectors for positioning mode operation, and one or more additional detectors for other operating modes.

Light conditioning optics 106 can include elements such as bandpass filters that are employed together with light source 102 in order to produce light used in positioning mode that is outside the detector system's fluorescence detection region and/or does not induce fluorescence in the specimen. For example, detector systems configured to measure fluorescence signals can be very sensitive due to the relatively weak intensity of many fluorescence emissions. Positioning mode light at a wavelength in the fluorescence measurement region of the detector system may be too intense and may damage optical elements in the detector system. Positioning mode light that induces fluorescence of a specimen may produce background signal in reference images and may also produce fluorescence emission that saturates the detector system. Accordingly, filters such as neutral density filters can be used to attenuate the intensity of the light incident on detector system 118. Alternatively, a less-intense light source element can be used in light source 102 to provide the light used in positioning mode.

Light conditioning optics 106 can further include optical elements designed to modify the spatial intensity profile of the light used in positioning mode, in order to provide for structured illumination. These optical elements are discussed in more detail below in connection with the structured illumination mode of operation.

Multiple Viewing Mode and Detection System

Figure 4:
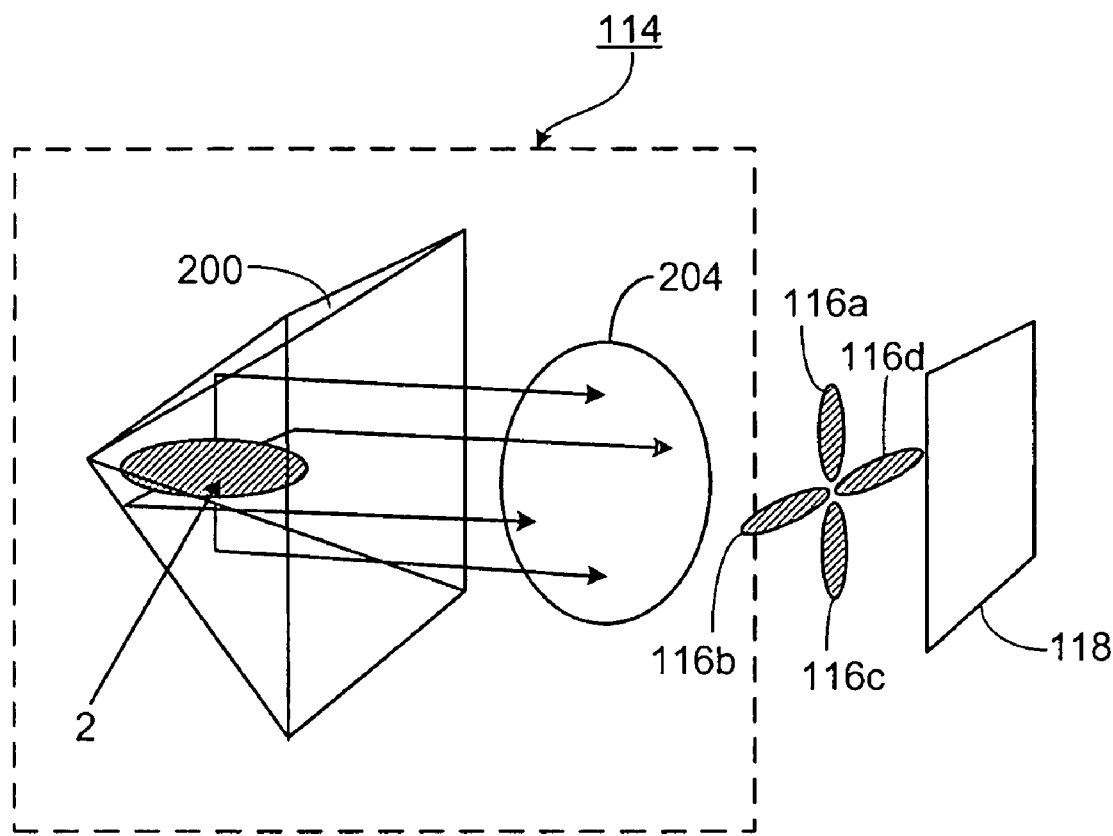
FIG. 4 is a schematic diagram of one embodiment of light collecting optics for acquiring multiple views of a specimen.

Light collecting optics 114 can be configured to capture one or more views of a specimen, and can include an optical element having multiple reflective surfaces, the element positioned and oriented with respect to the specimen in order to capture the multiple views. One embodiment of this optical element is a four-sided pyramid 200 shown in FIG. 4. In the embodiment shown, the pyramid is nominally a 90-degree, four faceted pyramid with internal surfaces that function as mirrors to project four side views of a specimen 2 to a lens and, eventually, to detector system 118. As shown in FIG. 4, the pyramid is oriented so that its axis of symmetry and a long axis of an extended specimen coincide. A single imaging lens 204 transfers the multiple side views 116$a$-$d$ of the specimen to detector system 118. Imaging lens 204 and detector system 118 are nominally oriented such that they view the extended specimen from an end-on direction, along the symmetry axis of pyramid 200.

In some embodiments, the apex of pyramid 200 may be removed to provide for back-illumination of the specimen. For example, white light illumination of the specimen from a position opposite detector system 118 can be used for profilometry or topographic imaging of the specimen. Removal of the pyramid's apex can also provide an access port for insertion of the specimen, for example.

In general, the angle of pyramid 200 does not need to be 90 degrees, and could be greater or less than 90 degrees to accommodate different measurement modes and optical elements in light conditioning optics 106 and light collecting optics 114. Pyramid 200 may be fabricated from any material suitable for fabrication of optical components such as, for example, BK7 glass or fused silica. In some embodiments, one or more surfaces of pyramid 200 may be coated with a material in order to enhance the reflectivity of the coated surfaces and/or to impart dichroic properties to the coated surfaces.

Pyramid 200 may, in general, have more than 4 angled, reflecting sides (e.g., 5 or more sides, 6 or more sides, 10 or more sides). If pyramid 200 includes more than 4 sides, measurement system 100 may be configured to capture more than 4 views of a specimen, since each reflective side of pyramid 200 can capture a view of the specimen. In general, the sides of pyramid 200 can also be curved, and the curvature may enhance the ability of pyramid 200 to direct light toward detector system 118. In some embodiments, a pyramid 200 having curved sides may obviate the need for one or more imaging lenses such as lens 204 in light collecting optics 114. Curved pyramid surfaces can also provide light collecting interfaces that correspond better to the surface of a specimen than flat light collecting surfaces would, and can therefore provide more sharply focused specimen views on a detector.

A general feature of embodiments of pyramid 200 is that the multiple views 116 of a specimen captured by pyramid 200 can be focused to a common focal plane at the position of detector system 118 by a lens or lens system such as lens 204, because the optical path lengths of the light from each of the views 116 are about the same due to the symmetry of the specimen position with respect to pyramid 200. This feature provides for higher resolution imagery and greater accuracy than would otherwise be possible in a measurement system where the optical path lengths of multiple views differed substantially.

In some embodiments, light conditioning optics 106 and light collecting optics 114 can share one or more common elements. For example, pyramid 200 can be used in both of these measurement system components. In one aspect, the reflective sides of pyramid 200 can be used to direct illumination light from a source to be incident on a surface of the specimen, for example. In another aspect, the reflective sides of pyramid 200 can be used to capture and direct multiple views of the specimen to a detector system.

Light collecting optics 114 transfer one or more views 116 to detector system 118, which captures and records each of the views simultaneously or sequentially. Detector system 118 may also convert each of the views to electronic signals 120. Detector system 118, in general, can include one or more detectors. If more than one detector is present, then in some embodiments, each one of the detectors can be configured to capture one of the multiple views 116 of a specimen, and each detector can be positioned in the image plane for the particular view it captures.

In some embodiments, detector system 118 may include imaging detectors such as CCD arrays and non-imaging photodetectors such as photodiodes and/or photomultiplier tubes. The non-imaging photodetectors can be used for light integrating measurement modes, such as whole specimen integration mode (to be described subsequently), and the imaging detectors can be used to capture views of the specimen.

Figure 5A:
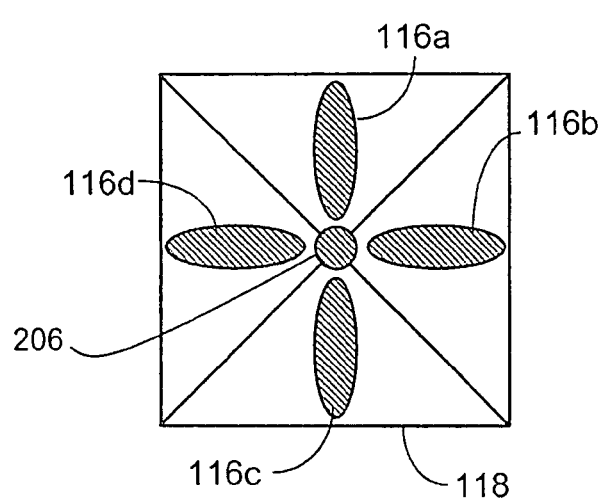
FIG. 5 is a schematic diagram showing two different orientations of multiple views of a specimen imaged onto the surface of a detector.
Figure 5B:
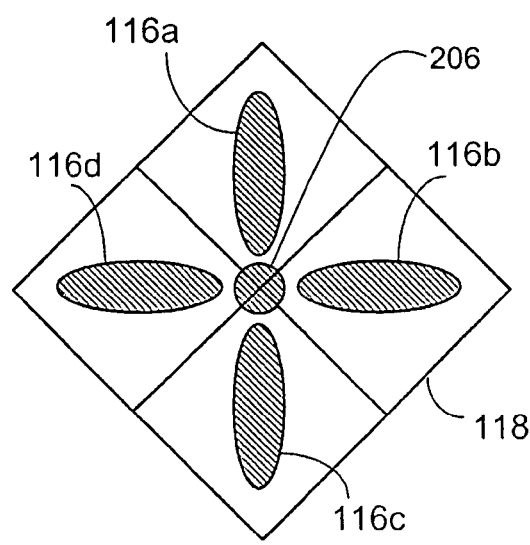

In some embodiments, detector system 118 may include a single imaging detector such as a CCD array, and all of the measured views of the specimen can be projected thereon by light collecting optics 114. For example, FIG. 5 shows an embodiment wherein a single CCD detector is used to capture four side views 116a-d and an end-on profile view 206 of a specimen. The views may be captured simultaneously or in any sequential arrangement. The profile view 206 can be used to provide additional information, such as boundary conditions, to 3D reconstruction models for the determination of specimen morphology.

Detector system 118 can generally be configured to record images produced from collected light that originates from different sources and/or emission mechanisms. For example, measurements may include projecting multiple views of a specimen onto one or more detectors, the images derived from illumination of the specimen with a white light or other broadband light source. Measurements can also include fluorescence emitted by the specimen in response to illumination light from a different light source such as a narrowband light source, or bioluminescence emitted by the specimen. Detector system 118 can be configured to simultaneously record measurement signals derived from multiple-source illumination of the specimen. Further, detector system 118 can be configured to monitor a specimen and provide a live view of the specimen during insertion, positioning and orientation, and removal from the measurement system. The live view of the specimen can be displayed for a system operator, for example, when operating in positioning mode as discussed above.

In some embodiments, detector system 118 may further be time-gated in order to measure temporal information from a specimen, such as time-of-flight scattering or fluorescence emission lifetime. This information can complement other measurement data and further guide 3D reconstruction algorithms. For example, static imaging measurements (i.e., with no time-gating) can be performed using a coherent or incoherent continuous wave (CW) light source element such as a CW laser, a photodiode, or a lamp. Dynamic, or time-domain, measurements can be performed, in some embodiments, using a coherent or incoherent pulsed light source element that is temporally synchronized with an electronic gating signal provided to detector system 118.

Electronic signals 120 corresponding to measurement signals and views captured by detector system 118 may be further processed using, for example, one or more mathematical algorithms implemented in electronic control system 122 to derive information about a specimen. In general, electronic control system 122 is electronically coupled to detector system 118 and implements algorithms such as 3D reconstruction algorithms to which the measured information serves as input. Reconstruction algorithms may, for example, use the information contained in multiple views of a specimen to construct a model of the internal structure of the specimen. Algorithms may use threshold or edge detection projections, along with other known image processing techniques, in order to improve input information or extract particular information from measured data.

Multiple-Wavelength Illumination Mode

In another mode of operation, measurement system 100 can be configured so that illumination light 108 provides multiple illumination wavelengths. In optical imaging of biological specimens, it is often useful to acquire information about structural entities located in the interior of a specimen. For example, information about the size and position of a tumor within an animal such as a mouse may be useful in both the diagnosis and treatment of disease and the testing of pharmaceutical agents. In particular, it may be especially advantageous to establish the position of a sub-surface entity within the specimen.

Fluorescence imaging is a useful technique for acquiring such depth or position measurements. Sub-surface entities can be labeled with a fluorescent moiety using either molecular biological or chemical techniques. Excitation light from a light source is absorbed by the fluorescent moieties, which then emit fluorescence. In general, fluorescence emission occurs at a wavelength different from the wavelength of the excitation light, providing a spectral emission optical signature that is different and separable from the excitation light source. Two proteins that can be expressed in biological structures of interest are green fluorescent protein (GFP) and red fluorescent protein (RFP).

Depth or position information can also be used to correct other measured data for scattering and absorption of emitted radiation by specimen tissues. Therefore, acquisition of this information can also be used to improve the accuracy of other measurements made with measurement system 100.

In general, biological tissues are turbid media that attenuate incident light by means of scattering and absorption. The attenuation factor scales with the thickness of the tissue, and therefore a measurement of emitted radiation from a specimen that includes a tissue layer, when compared with a measurement of emitted radiation from a similar specimen without the tissue layer, can be used to determine the tissue layer thickness. For example, if the specimen includes a sub-surface structural entity that is labeled with a fluorophore, measurement of the emitted fluorescence intensity from the structural entity and comparison to a calibrated emission standard for the same fluorophore in the absence of specimen tissue can be used (i.e., via a calibration table) to determine the thickness of tissue through which the emitted fluorescence radiation has passed, and therefore the depth of the structural entity below the surface of the specimen. If the same measurement is performed in two or more directions, the position of the structural entity within the specimen can be determined.

Unfortunately, radiation—either incident or emitted—also undergoes wavelength-dependent processes on passing through biological tissues, which change the overall spectral distribution of the radiation. It is often difficult to predict the magnitude of this shift at specific wavelengths for a particular sample, as different biological tissues produce different perturbative effects. The use of two or more incident wavelengths provides a means to correct measurement data for tissue thickness-dependent wavelength shifts in order to obtain better estimates of tissue thickness using the techniques described above.

Figure 6A:
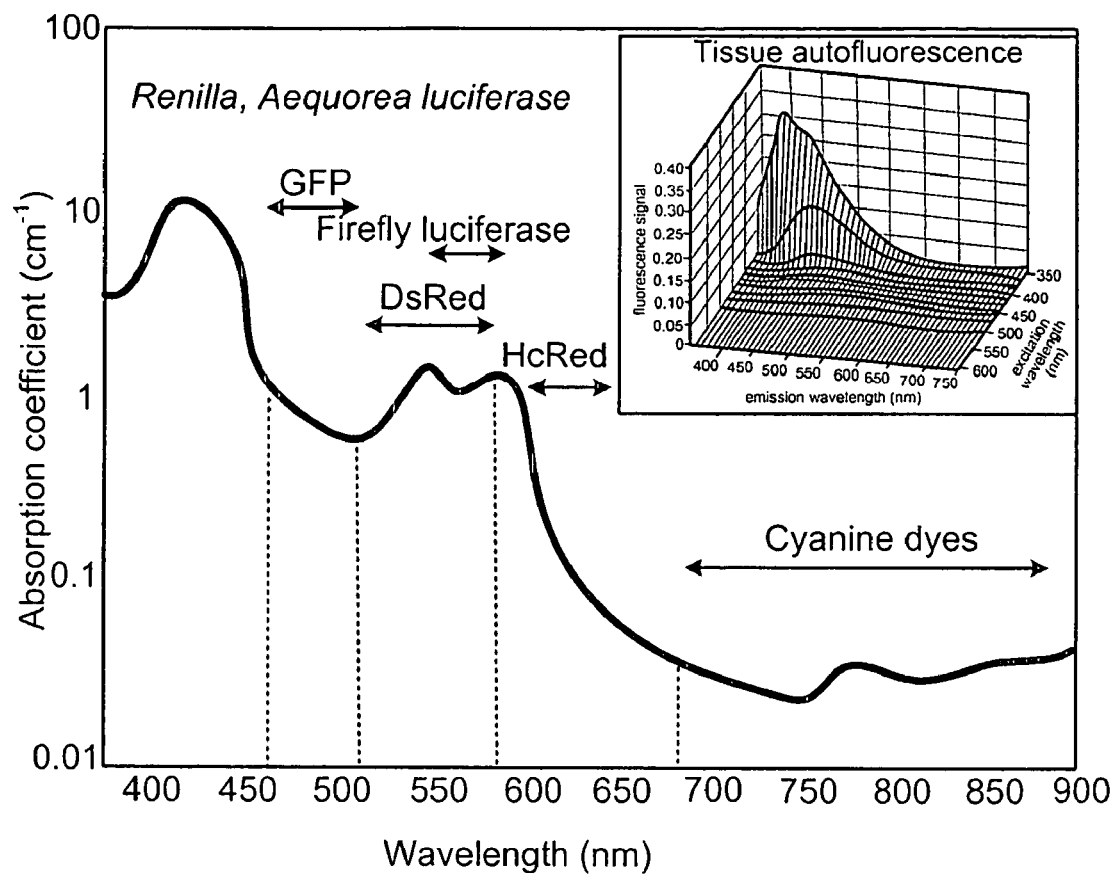
FIG. 6A is a plot showing the variation of the absorption coefficient for biological tissues with the wavelength of incident radiation.

An advantage of multiple-wavelength illumination, which provides spectral resolution in the measurement data on the excitation side, derives from the variation of the absorption coefficient of specimen tissues with the wavelength of radiation incident on the tissues, as shown in FIG. 6A. In general, better resolution in measured data is achieved when measurements are performed in spectral regions where the absorption coefficient varies more strongly with wavelength, such as in the region from about 600 nm to about 700 nm. One approach to acquiring spectral information is to provide a single source and to spectrally resolve the emitted fluorescence. However, light emitted via fluorescence is red-shifted relative to excitation light, and therefore, in order for the fluorescence emission to appear in a region from 600-700 nm, for example, the excitation light has a shorter wavelength. Unfortunately, the tissue absorption coefficient at shorter wavelengths, such as 550 nm for example, is considerably larger, so that the excitation light is strongly attenuated before reaching the fluorophores. As a result, the fluorescence signal can be relatively weak.

In contrast, by providing spectral resolution on the excitation side via a multiple-wavelength illumination source, the multiple source wavelengths can be selected to be in a suitable spectral region, such as the 600-700 nm region. The emitted fluorescence radiation will appear in a wavelength region that is red-shifted such as, for example, the near-infrared region. As a result, the illuminating radiation will be subject to an absorption coefficient in specimen tissues that is smaller than, for example, the absorption coefficient at 550 nm and as a result, radiation of higher intensity is delivered to the specimen, producing a stronger fluorescence signal.

Typically, in fluorescence optical imaging, tissue autofluorescence limits measurement sensitivity. Autofluorescence exists even when tissue is excited at near-infrared wavelengths. In the visible region, autofluorescence often overwhelms fluorescence emission of interest from labeled internal structures. In some cases, however, measured emission signals from a specimen can be acquired and used to separate signals specific to the internal entity under study from background signals due to tissue autofluorescence using spectral analysis tools such as linear spectral unmixing and principal component analysis. The autofluorescence spectrum of a typical tissue sample is shown, for example, in the inset of FIG. 6A.

A particular advantage of multiple wavelength illumination of a specimen is the ability to remove the autofluorescence signal from measured data. In general, a 2D fluorescence emission image of a specimen includes a 2D array of pixels. The fluorescence spectrum at any spatial position (i.e., any pixel location) in the image is given, to a first approximation, by a weighted linear sum of a fluorescence emission spectrum from a labeled entity of interest within the specimen and an autofluorescence spectrum of the specimen. If the two basis functions, i.e., the pure fluorescence emission spectrum from the labeled entity and the pure autofluorescence spectrum of the specimen are known, then a simple matrix inversion can be used to determine the weighting coefficients, and the autofluorescence spectrum can be mathematically subtracted from the measured spectrum at each pixel.

In some cases, only one of the basis functions—usually the pure autofluorescence spectrum—may be known. Spectral unmixing techniques can still be applied, even on a pixel-by-pixel basis, to the measured data. One procedure for unmixing label fluorescence and autofluorescence involves subtracting multiples of the autofluorescence spectrum from the measured fluorescence spectrum, until the lowest spectral intensity at any wavelength in the measured spectrum reaches zero. The difference spectrum that remains represents the pure fluorescence spectrum of the labeled entity.

Under some conditions, neither of the fluorescence component basis functions are known. Spectral unmixing techniques used in these situations are disclosed, for example, in U.S. patent application Ser. No. 10/669,101 entitled "SPECTRAL IMAGING OF DEEP TISSUE" by Richard M. Levenson et al., filed on Sep. 23, 2003, and in PCT Patent Application PCT/US2004/0316 entitled "SPECTRAL IMAGING OF BIOLOGICAL SAMPLES" by Richard M. Levenson et al., filed on Sep. 23, 2004 and published as WO 2005/040769. Both of the preceding applications are incorporated herein by reference.

Figure 6B:
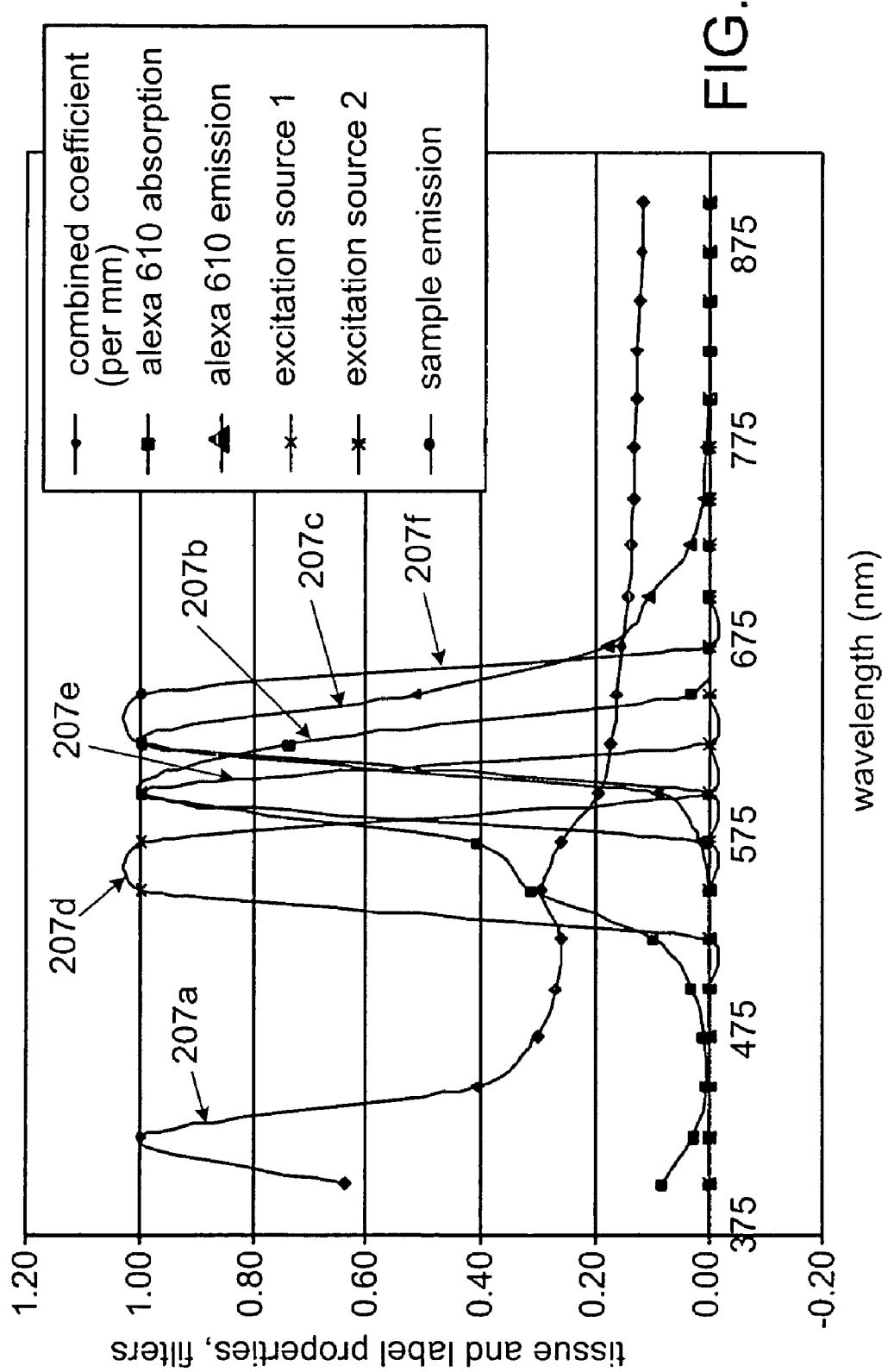
FIG. 6B is a plot showing the results of a simulation of a multiple excitation wavelength fluorescence measurement.

FIG. 6B is a plot showing the results of a simulation of the spectral shapes of various excitation and emission bands involved in a typical multiple wavelength excitation mode fluorescence measurement. The simulation uses the fluorescent label Alexa Fluor™ 610 (Molecular Probes, 29851 Willow Creek Road, Eugene, Oreg. 97402). Curve 207a shows the wavelength dependence of the tissue absorption coefficient. Curves 207b and 207c show the absorption and emission bands of the label, respectively, with the emission band red-shifted relative to the absorption band. Curves 207d and 207e show the wavelengths and bandwidths of the two excitation sources used in the simulated measurement. The wavelengths of the two excitation light sources are separated by about 50 nm. Curve 207f shows the combined fluorescence emission signal from the label due to excitation at both wavelengths (i.e., with sources having spectral bandshapes 207d and 207e) simultaneously. The emission signal 207f is centered in a region of the spectrum where tissue absorption is relatively weak, and therefore the intensity of fluorescence band 207f can be relatively high in some embodiments.

Figure 7:
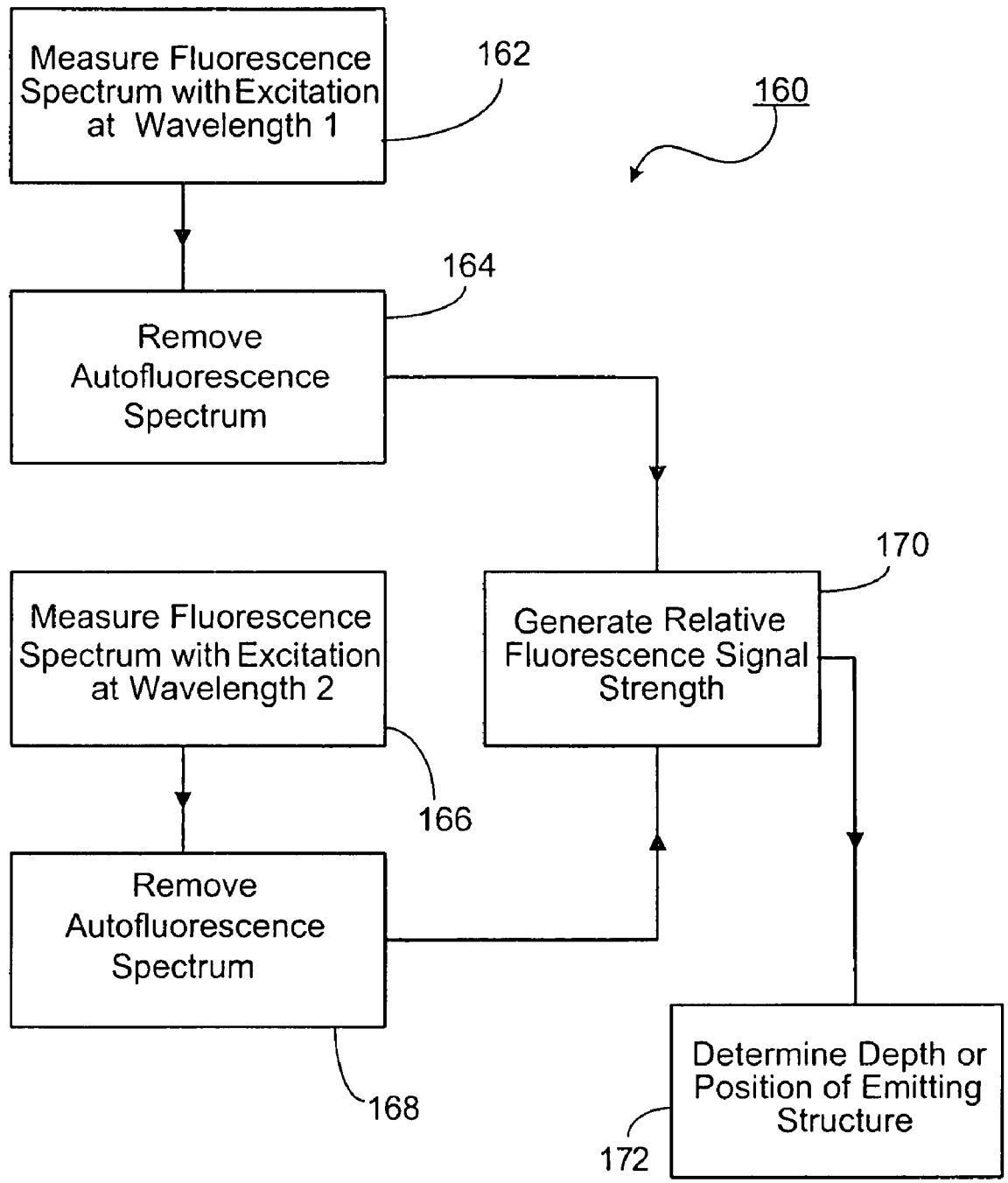
FIG. 7 is a flow chart that includes steps for making depth or tissue thickness measurements using multiple excitation wavelengths.

FIG. 7 is a flow chart 160 that summarizes steps in measuring the depth or position of a structural entity, such as a structure labeled with fluorophores in a specimen, using a multiple wavelength illumination source. The first step 162 includes measurement of a fluorescence spectrum from the specimen in response to excitation light at a first wavelength. In an optional second step 164, the autofluorescence spectrum may be removed from the fluorescence spectrum measured in first step 162 in order to correct the measured data. The third step 166 includes measuring a fluorescence spectrum from the specimen in response to excitation light at a second wavelength different from the first wavelength, and may be performed in sequence with first step 162. The fourth step 168, which is also optional, includes correction of the data measured in step 166 by removing the component of the measured spectrum that arises from tissue autofluorescence. In a fifth step 170, the two fluorescence signals are compared to produce a spectrum of relative fluorescence strength.

In general, a number of different techniques can be used in step 170 to compare and/or combine the fluorescence spectra obtained at two or more different excitation wavelengths. Using the example shown in flow chart 160 for two distinct excitation wavelengths, two corrected spectra are obtained as a result of the steps shown: $I_c(\lambda_1)$, the corrected fluorescence emission spectrum (i.e., with specimen autofluorescence removed) for excitation at wavelength $\lambda_1$; and $I_c(\lambda_2)$, the corrected fluorescence emission spectrum for excitation at wavelength $\lambda_2$. The ratio of the spectral intensities at a specific wavelength $\lambda$ is denoted $I_c(\lambda_1; \lambda)/I_c(\lambda_2; \lambda)$. The ratio of the spectral intensities in a pure sample of the fluorescent label excited at wavelengths $\lambda_1$ and $\lambda_2$ (i.e., without any intervening scattering medium such as tissue) is generally known or can be measured, and provides a reference ratio denoted as $I_r(\lambda_1; \lambda)/I_r(\lambda_2; \lambda)$. Step 172 then involves comparing the measured spectral intensity ratio $I_c(\lambda_1; \lambda)/I_c(\lambda_2; \lambda)$ to the known reference spectral intensity ratio $I_r(\lambda_1; \lambda)/I_r(\lambda_2; \lambda)$ in order to obtain a measurement of the depth of the emitting structure below the surface of the specimen or, in other words, a tissue thickness. In some embodiments, for example, step 172 includes taking a ratio of the quantities $I_c(\lambda_1; \lambda)/I_c(\lambda_2; \lambda)$ and $I_r(\lambda_1; \lambda)/I_r(\lambda_2; \lambda)$ for purposes of comparison. A look-up table or other means such as a mathematical algorithm can be used to transform the quantity $I_c(\lambda_1; \lambda)/I_c(\lambda_2; \lambda)$ into a thickness. The measured and reference spectral intensity ratios may be compared at a single wavelength $\lambda$ in order to determine a thickness, or the intensity ratios at a number of selected wavelengths, or even at all measured wavelengths in the spectra, may be compared and averaged to obtain an estimate of tissue thickness. In some embodiments, the properties of the specimen may dictate that particularly accurate measurements are obtained by considering the intensity ratios at a known subset of specific wavelengths, and therefore the measured and reference intensity ratios at these wavelengths may be preferentially selected for comparison in order to estimate tissue thickness.

Frequently, depth or thickness measurements derived from combining spectral data obtained at multiple excitation wavelengths, as shown in step 170, are more accurate than measurements derived from single excitation wavelength fluorescence emission. The sequence of steps in flow chart 160 can be further repeated for illumination along two additional directions, each orthogonal to the other and orthogonal to the first illumination direction, in order to determine the 3D position of the structural entity within the specimen.

In general, the measurement procedure shown in FIG. 7 can include more than two illumination wavelengths. For example, three or more wavelengths (e.g., four or more wavelengths, five or more wavelengths, ten or more wavelengths) can be used, and the measured fluorescence signals due to excitation at each of the excitation wavelengths may be combined in any desired manner in step 170 in order to provide more accurate depth or tissue thickness measurements. The excitation wavelengths may further be chosen to be as far apart as desired, provided excitation light at each wavelength induces a measurable fluorescence emission signal in the specimen.

Measurement system 100 can be configured to provide for multiple wavelength illumination of a specimen under study. Light source 102 can include, for example, two different light source elements, configured to produce light at different selected wavelengths, where the wavelengths are chosen to provide accurate measurement signals. In some embodiments, light source 102 can include light source elements that provide light at three or more excitation wavelengths (e.g., four or more wavelengths, five or more wavelengths, ten or more wavelengths). The light source elements that provide the excitation wavelengths can be separate elements, each configured to provide light at a chosen wavelength. Alternatively, in some embodiments, the light source can include a single broadband light source element, and light conditioning optics 106 can include a series of optical elements configured to produce excitation light having different wavelength components. For example, light conditioning optics 106 can include active filter elements such as liquid crystal tunable filters, passive filter elements such as bandpass filters, and beam directing optics such as beamsplitters, mirrors, and the like. In some embodiments, for example, the light conditioning optics 106 and light collecting optics 114 may share some common optical elements; that is, the optical paths traversed by the excitation light and by the emitted light (i.e., fluorescence) may be partially collinear, the two paths separated eventually by an element such as a dichroic beamsplitter. Such a configuration is referred to as epi-fluorescence measurement. In other embodiments, the optical paths of the excitation light and the emitted fluorescence are not collinear. Light collecting optics 114 can be configured to capture one or more views of the specimen under study, and can include, for example, imaging elements such as lenses and light gathering optics such as pyramid 200.

Multiple Wavelength Emission Mode

Measurement system 100 can also be configured to operate in a multiple wavelength emission mode. As discussed above in connection with the multiple wavelength illumination mode, radiation such as fluorescence emitted from a specimen can be captured and spectrally resolved in order to provide an estimate of the depth of an emitting structural entity below the surface of a specimen or, in three dimensions, the internal position of the entity within the body of the specimen.

Typically, fluorescence imaging techniques estimate thicknesses of scattering tissues by measuring an attenuation factor for emitted fluorescence radiation and comparing the intensity of the emitted radiation to the known intensity for the fluorescent label of interest in the absence of scattering tissues. However, emitted radiation such as fluorescence also undergoes a wavelength shift on passing through scattering media such as specimen tissues, and because the absorption coefficient of the tissue is wavelength dependent, tissue thickness-induced wavelength shifts can produce errors in tissue thickness estimates that arise from uncompensated variations in the absorptive properties of the tissues.

Multiple wavelength emission mode provides a means for correcting measured data to account for wavelength dependent absorption properties of biological tissues. As discussed previously, fluorescent labels or moieties can be introduced into a specimen using molecular biological or chemical means and localized in an internal structural entity of interest. In the present mode of operation of system 100, multiple different fluorescent labels of interest are introduced into the structural entity, each label type having a different emission band. When the specimen is illuminated with light from a source, fluorescence emission is induced from each of the fluorescent labels and is captured using light collecting optics 114 and detector system 118.

The fluorescence emission signals at multiple emission wavelengths provide complementary data concerning the thickness of tissues through which the fluorescent light has passed. When the data are combined in order to correct for wavelength dependent absorption properties of specimen tissues, a more accurate estimate of tissue thickness than would otherwise result from using only a single distinct fluorescent label may be obtained. When only one type of fluorescent label is introduced into the structural entity of interest, the differential absorption between two different wavelengths in the emission band of the label is usually too small to realize accurate depth measurements. Corrections to depth measurements that are based on determining ratios of fluorescence emission signals at different wavelengths are not as effective because the wavelengths must necessarily both fall within the emission band of the fluorescent label. In contrast, when multiple fluorescent labels are used, the labels can be chosen such that their emission bands are spectrally separated (e.g., 75 nm apart, 100 nm apart, 150 nm apart, 200 nm apart, 500 nm apart). For such a large separation in emission wavelengths, the differential tissue absorbance at the emission wavelengths is typically much larger than in singly-labeled specimens, so that corrections to depth measurements that are based on ratios of fluorescence emission signals are more effective, and depth measurements are more accurate.

The present mode of operation permits any number of distinct fluorescent labels to be introduced into the specimen. For example, structural entities within the specimen can be labeled using two or more distinct fluorescent moieties (e.g., three or more distinct fluorescent moieties, five or more distinct fluorescent moieties, ten or more distinct fluorescent moieties). As an example, where two distinct fluorescent moieties are introduced into a specimen, the two fluorescent labels may be bound to or expressed by the same target location (i.e., a structural entity of interest) in known proportion. A fluorescence label mixture can be engineered to have spectral fluorescence characteristics tailored to take advantage of spectral variations of scattering efficiency and tissue absorption in order to accurately determine the depth or position of the structural entity.

Figure 8:
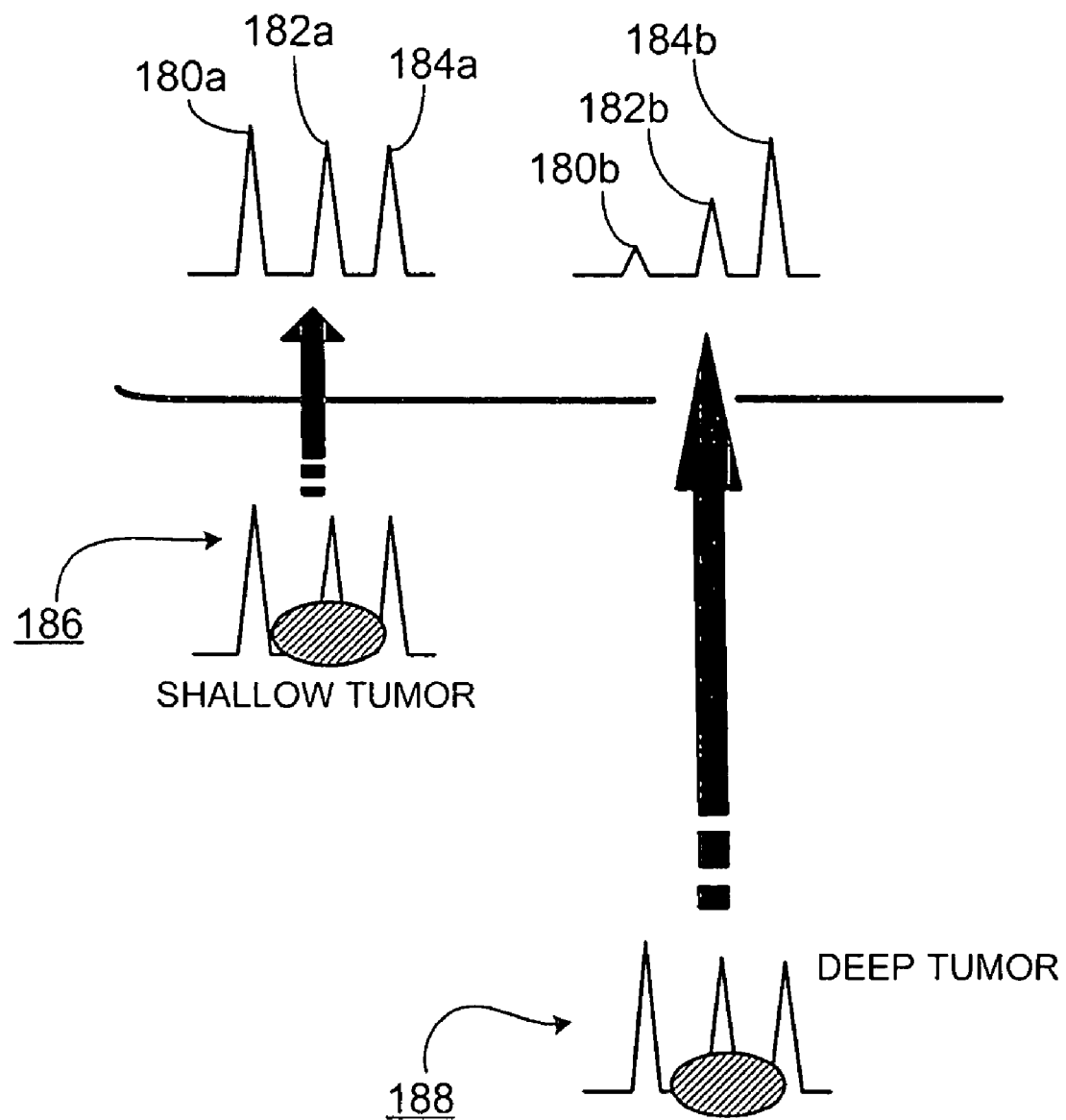
FIG. 8 is a schematic diagram showing wavelength-dependent attenuation of fluorescence radiation emitted by a labeled specimen.

FIG. 8 is a schematic diagram showing wavelength dependent attenuation of emitted fluorescence signals from a specimen. A light source (not shown) is first used, on the left hand side of the figure, to illuminate a structural entity such as a tumor located at a relatively shallow depth below the surface of the specimen. The tumor is labeled with three different fluorophores having fluorescence emission bands centered at 500 nm, 625 nm, and 750 nm, respectively. As discussed previously, absorption by specimen tissues varies according to wavelength and is typically stronger at shorter wavelengths. For a shallow tumor emitting fluorescence 186 at each of these three wavelengths, the attenuation of the fluorescence intensity due to tissue absorption at each wavelength is relatively small. Band 180a at 500 nm is not attenuated to a significantly larger extent than either band 182a at 625 nm or band 184a at 700 nm. Illumination of a deep tumor, located well below the surface of the specimen as shown on the right hand side of the figure, induces emission of fluorescence 188. After propagating through a relatively larger thickness of tissue, the intensity of band 180b at 500 nm is more strongly attenuated than the intensity of band 182b at 625 nm or band 184b at 700 nm, due to the larger tissue absorption coefficient at shorter wavelengths. It is clear from the relative intensities of the fluorescence emission bands that depth estimates based on only a single emission wavelength will vary depending on the chosen wavelength due to the wavelength dependent absorption properties of specimen tissues.

Figure 9:
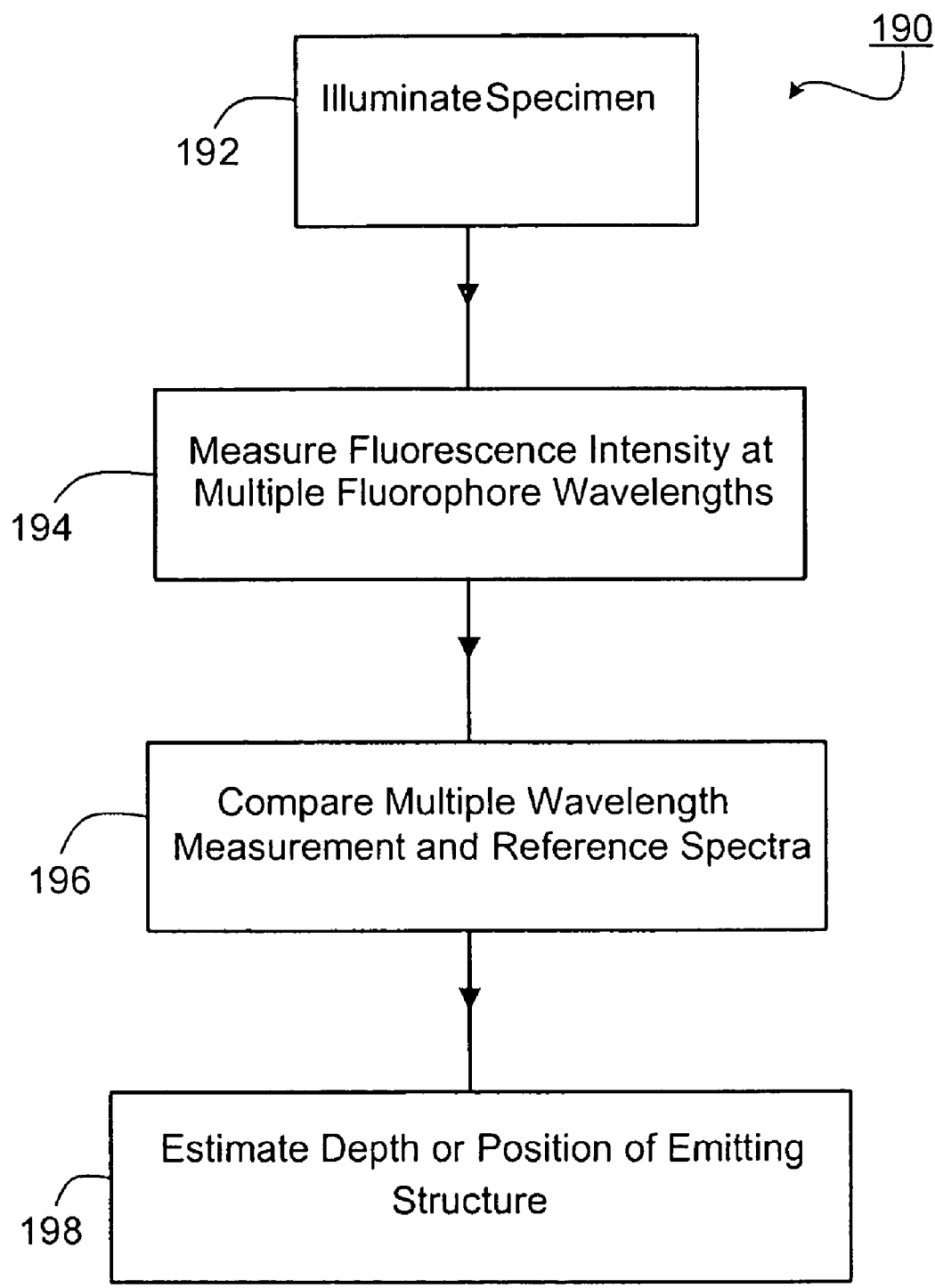
FIG. 9 is a flow chart that includes steps for making depth or tissue thickness measurements using multiple fluorescent labels in a specimen.

FIG. 9 is a flow chart 190 that shows a series of measurement steps for making multiple wavelength emission measurements to determine the depth or position (i.e., tissue thickness) of a light emitting structural entity within a specimen. In a first step 192, a specimen labeled with multiple different types of fluorescent labels is illuminated with light from a source, inducing fluorescence emission from the labels. The labels are typically chosen such that the maxima in their respective emission bands are separated from one another spectrally. The second step 194 includes measurement of the simultaneous fluorescence emission signals from each of the distinct labels. Step 194 provides a total fluorescence spectrum, $I_t(\lambda)$ that includes the fluorescence emission spectra of each of the fluorescent labels scaled by the tissue absorption coefficient, $\sigma(\lambda)$. To a first approximation, the total fluorescence emission spectrum for three distinct labels 1, 2, and 3 having fluorescence emission maxima at $\lambda_1$, $\lambda_2$, and $\lambda_3$, respectively, may be written as $I_t(\lambda)=\sigma(\lambda_1)I_1(\lambda)+\sigma(\lambda_2)I_2(\lambda)+\sigma(\lambda_3)I_3(\lambda)$. In addition, a reference fluorescence spectrum corresponding to emission from the three labels in the absence of scattering tissue can be written as $I_r(\lambda)=I_1(\lambda)+I_2(\lambda)+I_3(\lambda)$. The third step 196 includes comparison of the measured multiple wavelength emission signal $I_t(\lambda)$ with the reference signal $I_r(\lambda)$. For example, the two signals may be ratioed at selected wavelengths or at all wavelengths in the spectra in order to produce a reduced multiple wavelength emission signal. If the two signals are ratioed or otherwise compared at multiple wavelengths, the results may be averaged, for example.

From the expressions for $I_t(\lambda)$ and $I_r(\lambda)$, it is evident that using a larger number of fluorescence labels in a specimen may provide more accurate measurement results, because the spectral intensity of the total measured fluorescence signal will have a broader distribution of high intensity regions.

The fourth step 198 includes providing an estimate of the depth of the entity below the surface of the specimen or, alternatively, the thickness of tissue through which the fluorescence emission signals have propagated, based on the comparison between the total measured and reference fluorescence emission signals (e.g., an averaged ratio of the two signals). The depth estimate can be obtained, for example, from a calibrated look-up table or from a mathematical algorithm that relates the ratio of the fluorescence signals to a calibrated depth measurement. The measurement cycle shown in flow chart 190 can be repeated from two additional, mutually orthogonal directions in order to determine a 3D position of the structural entity within the body of the specimen.

In order to provide an accurate calibrated depth measurement, some information regarding the concentration ratio of the various fluorescent labels in the specimen should be known. Once this knowledge is gained, small changes over time in the concentration ratios of the fluorescent labels have relatively little effect on measurements of depth, which are typically much more sensitive to tissue thickness.

In some embodiments, fluorophores are chosen to provide fluorescence emission signals that, when ratioed, either increase or decrease monotonically as a function of tissue thickness. This is helpful in avoiding depth determination ambiguities which might otherwise result from the dependence of the tissue absorption coefficient as a function of wavelength.

In some embodiments, at least one fluorescent label introduced into the specimen can have a fluorescence emission band centered at about 980 nm. A label having fluorescent emission near 980 nm can be used to determine the thickness of specimen tissues containing significant quantities of water.

In general, the techniques described in connection with multiple wavelength illumination mode can also be used in conjunction with multiple wavelength emission mode. For example, multiple distinct fluorescent probes can be introduced into the specimen, and multiple excitation wavelengths can be used to induce fluorescence at each of the emission wavelengths of the fluorophores. This may provide complementary information that can be used to further refine depth/thickness estimates, for example. In addition, the combination of both excitation- and emission-side spectral resolution may permit autofluorescence removal from the measured data, as discussed previously.

Measurement system 100 can be configured to provide for operation in multiple wavelength emission mode. In particular, light collecting optics 114 can include, for example, active spectral filtering elements such as liquid crystal tunable filters and/or passive filtering elements such as spectral bandpass filters, along with other optical elements for collecting and directing emitted light, such as dichroic beamsplitters, spectrally neutral beamsplitters, mirrors, and the like.

Whole Specimen Integration Mode

Most 3D non-optical imaging techniques provide 3D internal structure information in a specimen under study by resolving physical or structural variation. The volumes and physical dimensions of internal structures are often derived from detected structural boundaries between regions internal to the specimen that have specific differences in their physical characteristics.

Fluorescent labels specific to a particular structural feature of interest in a specimen, such as a tumor, can be readily introduced using previously discussed techniques. In the present mode of operation, under appropriate conditions, the total fluorescence radiation intensity emitted by a labeled structure can be correlated with the mass of the structure. For example, measurements of total fluorescence intensity from a tumor in a specimen such as a mouse can be used to estimate the mass of the tumor. In a measurement configuration designed to measure total fluorescence intensity, therefore, the specimen can act as an integrating sphere for emitted radiation.

Experimental work has shown that the mass of subcutaneous tumors located near the surface of a specimen can be tracked quantitatively by integrating the fluorescence emission signal on a single 2D image of the tumor, see for example F. E. Dieln et al., "Noninvasive fluorescence imaging reliably estimates biomass In-Vivo", *Biotechniques* 33: 1250-1255 (2002), the contents of which are incorporated herein by reference. In these situations, for example, the tumor is located a fraction of a millimeter from the specimen surface, and almost all of the emitted fluorescence escapes from the specimen in the immediate vicinity of the tumor, thereby facilitating detection using a single 2D image.

In general, however, if the structural entity of interest (i.e., a tumor) is positioned deeper inside the body of a specimen, single-view 2D imaging is often much less effective due to scattering of fluorescence emission in multiple directions. For example, in orthotopic tumors, fluorescence radiation escapes in all directions in difficult-to-predict ways due to inhomogeneous scattering, and the apparent integrated fluorescence signal derived from a single 2D image depends upon the angle of specimen observation.

In order to use emitted fluorescence to accurately measure the mass of a tumor or other labeled structural entity, the total emitted radiation flux from the tumor or entity should be nearly directly proportional to the mass of the tumor or entity. In addition, fluorescence at the measurement wavelength should generally be specific to the structure of interest, i.e., no other internal structures should act as significant sources of emitted light at the measurement wavelength. Further, the excitation and emission wavelengths should be selected so that absorption of the incident and emitted radiation by specimen tissue is sufficiently non-perturbative that these effects can be overlooked. Fluorescent moieties which satisfy these conditions include, for example, Cyanine dyes (Amersham Biosciences Corp., 800 Centennial Ave., Piscataway N.J. 08855-1327) and Alexa dyes (Molecular Probes, 29851 Willow Creek Road, Eugene, Oreg. 97402).

Removal of fluorescence intensity due to specimen autofluorescence can be especially important when operating in whole specimen integration mode, because the entire surface of a specimen will contribute a background autofluorescence signal, whereas fluorescence emission derived from a labeled structural entity is confined to a much smaller spatial volume region. Autofluorescence removal can be performed using the spectral decomposition techniques discussed previously, or using other non-spectral methods such as time-gating of the detector system.

Whole specimen integration mode, or whole mouse integration mode (when the specimen of interest is a mouse) can provide a speed advantage over other measurement techniques such as 3D structure determination via computational models. In whole specimen integration mode, the total emitted radiation flux from a particular view of the specimen can be measured without spatially resolving the intensity distribution. Thus, a single intensity index is obtained for each view of the specimen. Time-consuming 3D reconstruction algorithms are not employed to process measured fluorescence data.

In addition, scattering of fluorescence emission by specimen tissues poses fewer problems than in spatially-resolved measurement modes. Since emitted light from all regions of the specimen is integrated by the detector system, scattering events in tissue, which typically redistribute light in space, have a relatively small impact on the accuracy of the measured fluorescence intensity. Only if scattering events in tissues increase the average optical path length to the degree that tissue absorption becomes important will scattering pose a significant problem.

Measurement system 100 can be configured to operate in whole specimen integration mode. For example, detector system 118 can include one or more imaging detectors such as CCD cameras for capturing multiple views of specimen fluorescence. The spatially resolved fluorescence images captured by the detector system may each be integrated to provide a single integrated fluorescence intensity measurement for each captured view of the specimen. Alternatively, detector system 118 can include non-imaging photodetectors such as photodiodes and/or photomultiplier tubes for measuring integrated fluorescence from multiple views of a specimen. Light collecting optics 114 can include one or more lenses positioned to direct emitted fluorescence onto the active areas of such photodetectors.

In some embodiments, measurement system 100 can be configured to monitor a single view of a specimen and record a measurement of the total emitted fluorescence intensity measured in the monitored view. In other embodiments, measurement system 100 can be configured to monitor multiple views of the specimen. Integrated fluorescence intensity measurements from the multiple views can be combined to give a measurement of the total integrated flux of fluorescence from the entire surface of the specimen. This total integrated flux measurement can be used to determine, for example, a mass of a fluorescent entity internal to the specimen and giving rise to the measured fluorescence. In many cases, the mass of the entity determined using multiple views of the specimen is more accurate than a mass determined using only a single view of the specimen.

In some embodiments, multiple viewing mode can be used to collect multiple views of a fluorescing specimen, and the fluorescence intensity in each of the views can be integrated. For example, pyramid 200 in FIG. 4 can be used to collect fluorescence emission from multiple sides of a specimen. The images of the specimen can be directed to an array detector such as a CCD, imaged, and integrated electronically, for example. Alternatively, the light from each of the multiple views can be collected using mirrors, lenses, and other similar optical elements, and be directed onto a non-imaging detector such as a photodiode or a photomultiplier tube that produces a single measurement of the integrated fluorescence intensity.

Figure 10:
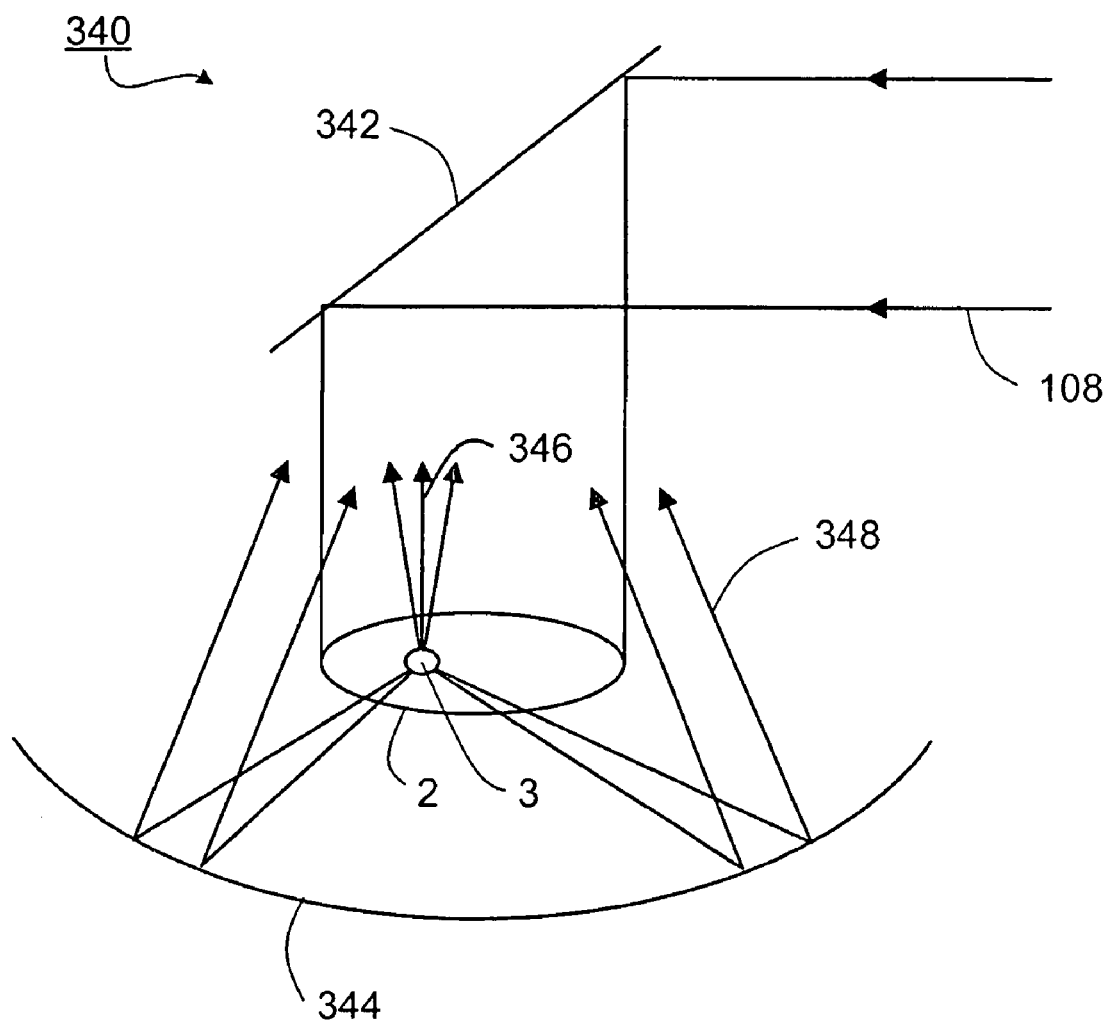
FIG. 10 is a schematic diagram of one embodiment of a measurement system operating in whole specimen integration mode.

Another embodiment of a measurement system 340 for performing integrated fluorescence measurements by collecting fluorescence emissions from multiple sides of a specimen is shown in FIG. 10. System 340 includes a reflecting surface 342 that directs illumination light 108 onto the surface of a specimen 2. A labeled entity 3 within specimen 2 emits fluorescence in all directions in response to illumination light 108. Some fluorescence rays, such as ray 346, are emitted in a direction that is substantially opposite to the direction of incidence of illumination light 108, and are directed by surface 342 to a detector system (not shown). Other rays, such as ray 348, are directed by reflecting surface 344 toward surface 342, and thenceforth to a detector system. In this embodiment, individual views of the specimen are not resolved, and all of the collected fluorescence emission is directed to a non-imaging detector. In general, system 340 can be a two dimensional system as shown in FIG. 10, or system 340 can be a three dimensional system in which surface 342 is one angled surface of a reflective pyramid such as pyramid 200, and surface 344 is a reflective surface of a concave mirror having a spherical, paraboloidal, or other suitable shape for collecting emitted fluorescence radiation. Either two-dimensional or three-dimensional systems can be configured to collect fluorescence radiation from multiple sides of a specimen.

As discussed previously, the measurements of integrated fluorescence intensity for each of the monitored views can be corrected using data obtained from measurement system 100 operating in another measurement mode. For example, depth/thickness measurements obtained in multiple wavelength illumination mode or in multiple wavelength emission mode can be used to calculate a correction factor to apply to integrated fluorescence intensity measurements in order to compensate for absorption of fluorescence radiation by specimen tissues.

Figure 11:
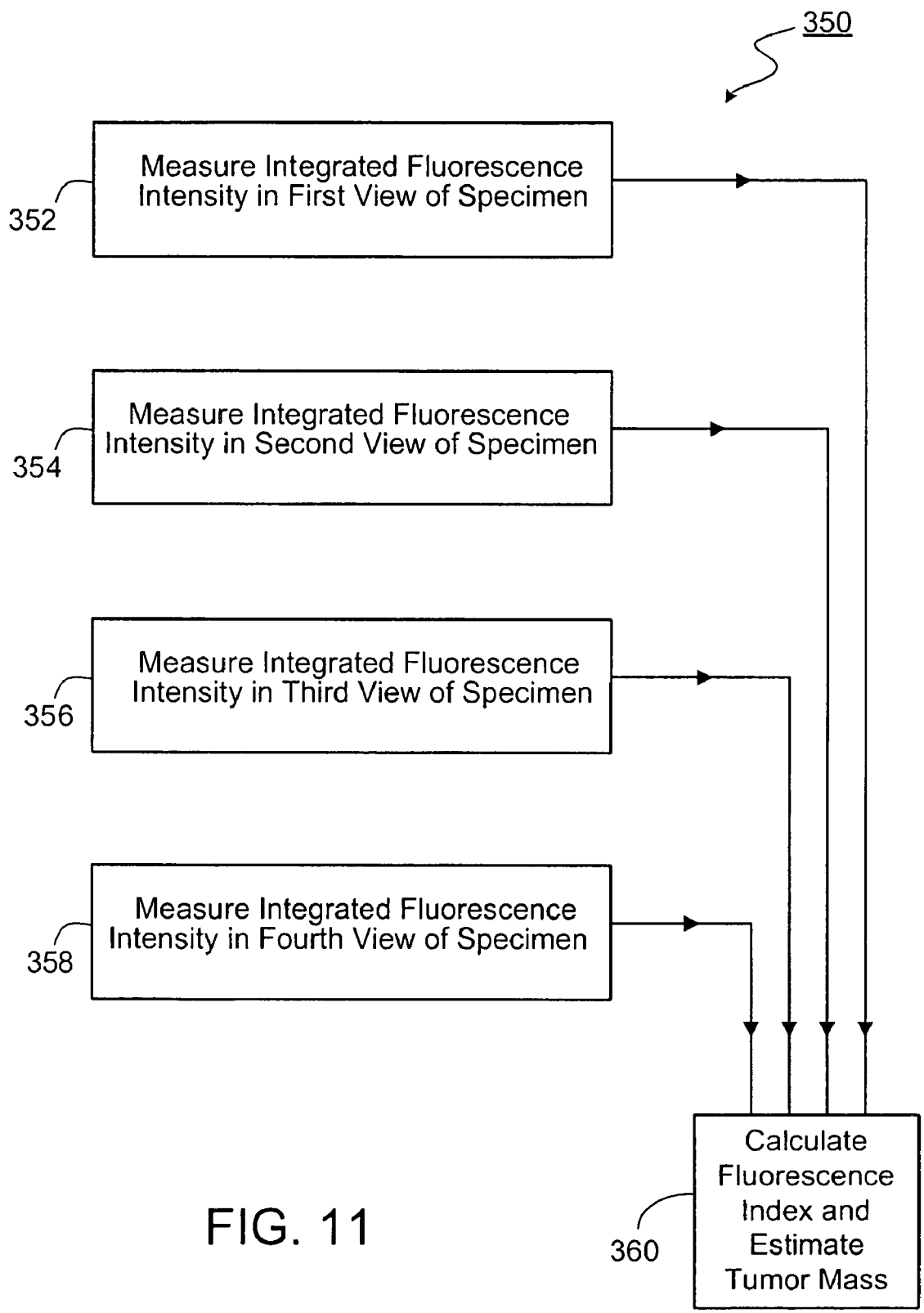
FIG. 11 is a flow chart that includes steps for estimating the mass of a structure, such as a tumor internal to a specimen, from integrated fluorescence measurements.

In many applications, a sufficiently accurate estimate of tumor mass (or, more generally, the mass of a structural entity) can be obtained by measuring a representative portion of the emitted flux of fluorescence photons from a labeled specimen. It is generally not necessary to capture every emitted photon. Steps for estimating the mass of a labeled tumor in a specimen such as a mouse are shown on flow chart 350 in FIG. 11. Steps 352, 354, 356 and 358 include measuring the total emitted fluorescence intensity in four different views of the specimen. The integrated fluorescence intensities from each of the views are combined in step 360 to produce a representative fluorescence emission index for the specimen. The fluorescence emission index is then used to estimate the mass of the labeled tumor. The combination of the fluorescence intensities from each of the views can be performed according to a formula or computer algorithm. For example, the total fluorescence intensities from each of the views can simply be added together to produce an overall total fluorescence intensity index. In some embodiments, scaling factors based on depth measurements performed using other operating modes of the measurement system can be used to produce a scaled linear combination of the integrated fluorescence intensities from each view of the specimen. Similarly, the determination of tumor mass from the index can be performed using a look-up table or a mathematical algorithm, for example.

One or more calibration steps can be performed initially and at selected intervals in order to correlate the fluorescence index with tumor mass. For example, in an initial calibration step, a fluorescence index can be determined for a particular specimen, and the specimen can subsequently be sacrificed in order to measure the mass of a labeled tumor directly. Further calibration steps can be performed periodically to validate and/or enhance the relationship between the predictive measured optical signal and the biological mass under study.

Structured Illumination Mode

Measurement system 100 can also provide an illumination light intensity profile that is either uniform or structured (e.g., a spatially varying illumination intensity profile and/or an illumination profile that is controlled in time sequence) at the specimen position. This provides different means to obtain structural and optical information from the specimen, the information serving as input to 3D reconstruction algorithms. The light source used for structured fluorescence excitation can include one or more light source elements such as conventional lamps, LEDs, or lasers, for example. The illumination light can be delivered to the specimen directly or via fiber optics, dichroic beamsplitters, light pipes, diffusers, or any other optical device to transport and/or condition the light.

For example, in some structured illumination modes of operation, different sides of a specimen can be illuminated in a chosen sequence. Moreover, each side of the specimen can be illuminated with a patterned light intensity profile, or with a sequence of light intensity patterns. Even a single light intensity pattern, used to illuminate one or more sides, can be used to realize the benefits of structured illumination. In general, structured illumination mode provides for either simultaneous illumination of a specimen with a structured light source, or direction-sequential illumination with a structured light source.

Figure 12:
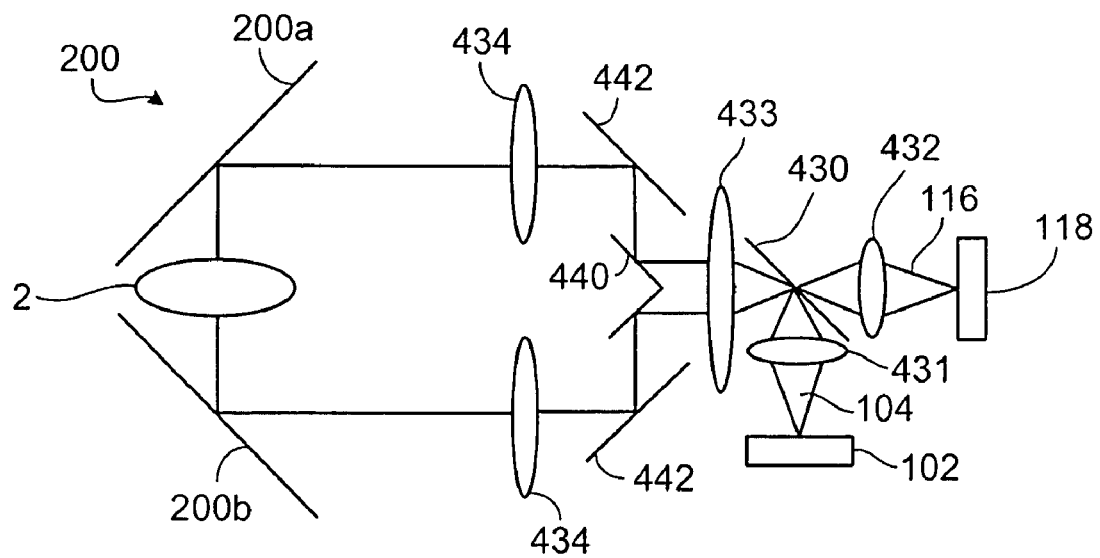
FIG. 12 is a schematic diagram showing an embodiment of a measurement system that includes a structured illumination source.

In a first aspect, structured illumination of a specimen can be provided by multiple light source elements arranged in a desired configuration around the specimen. For example, FIG. 12 shows an embodiment of a measurement system 100 that includes a source 102 configured to direct light 104 to a lens 431, which directs the light to reflect from a dichroic beamsplitter 430 and to pass through an imaging lens 433. The light is divided into two counter-propagating portions by mirror 440. One of the portions is directed to reflect from mirror 442, pass through lens 434, reflect from a first surface 200a of pyramid 200, and impinge upon specimen 2 from above in the plane of the figure. The second portion of the illumination light is directed to reflect from mirror 442, pass through lens 439, reflect from a second surface 200b of pyramid 200, and impinge on the specimen from below in the plane of the figure. The structured illumination provided by the two beams induces fluorescence in the specimen. Portions of the emitted fluorescence retrace the optical paths of the excitation beams to beamsplitter 430. Due the red-shift of the emitted fluorescence, the fluorescence radiation is transmitted through dichroic beamsplitter 430 and is imaged by lens 432 as two different views 116 of specimen 2. The two views are captured by detector system 118, which includes a CCD array. The embodiment shown in FIG. 12 is an epi-fluorescence measurement system, and the incident light and the emitted fluorescence encounter several optical elements common to the optical path of each.

FIG. 12 shows a two-dimensional projection of a three-dimensional measurement system. Therefore, optical elements that are not positioned in the plane of the figure are not depicted. For example, other surfaces of pyramid 200 are not shown in figure—these are used to capture other views of the specimen. In general, other light source elements, mirrors, beamsplitters, and other optical elements can also be present. For example, a second set of light conditioning and collecting optics can be used to capture two additional views of the specimen propagating into and out of the plane of FIG. 12. In some embodiments, the measurement system can be only two-dimensional, however, as depicted. Further, in some embodiments, surfaces 200a and 200b can be two surfaces of a mirror, or they can be the surfaces of two separate mirrors. In general, many combinations of optical elements can be provided in order to capture a two- or three-dimensional set of views of specimen 2. The foregoing discussion applies as well to the embodiments of FIGS. 13-16, any of which may be configured to operate in a two-dimensional or three-dimensional imaging modality.

Figure 13:
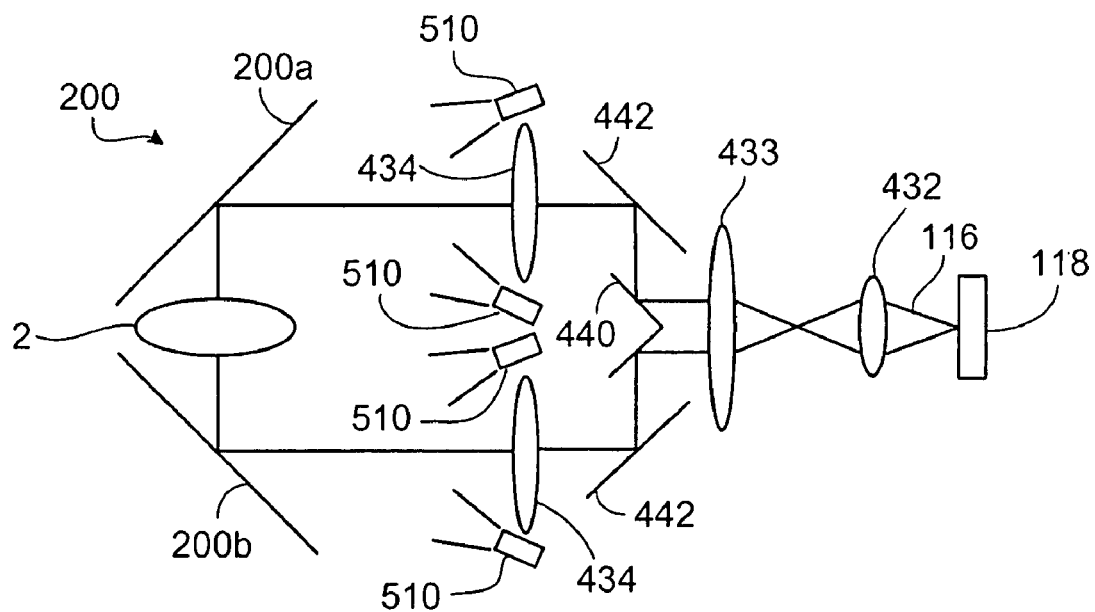
FIG. 13 is a schematic diagram showing an embodiment of a measurement system that includes a structured illumination source.

Another embodiment of a measurement system that provides a structured illumination source is shown in FIG. 13. In this embodiment, light provided by optical fiber bundles 510 arranged around specimen 2 is used to illuminate the specimen and induce fluorescence. The emitted fluorescence is collected by a series of optical elements that are similar to those of FIG. 12. Since the illumination and fluorescence radiation do not share a common optical path, the embodiment of FIG. 13 is an example of a non-epi-fluorescence measurement system. In this embodiment, for example, the fiber bundle source elements 510 can be positioned to illuminate different sides of specimen 2 via the reflective surfaces of pyramid 200. Further, each of the source elements 510 can be selectively enabled to provide direction-sequential illumination when desired, or the sources may all be simultaneously enabled.

Figure 14:
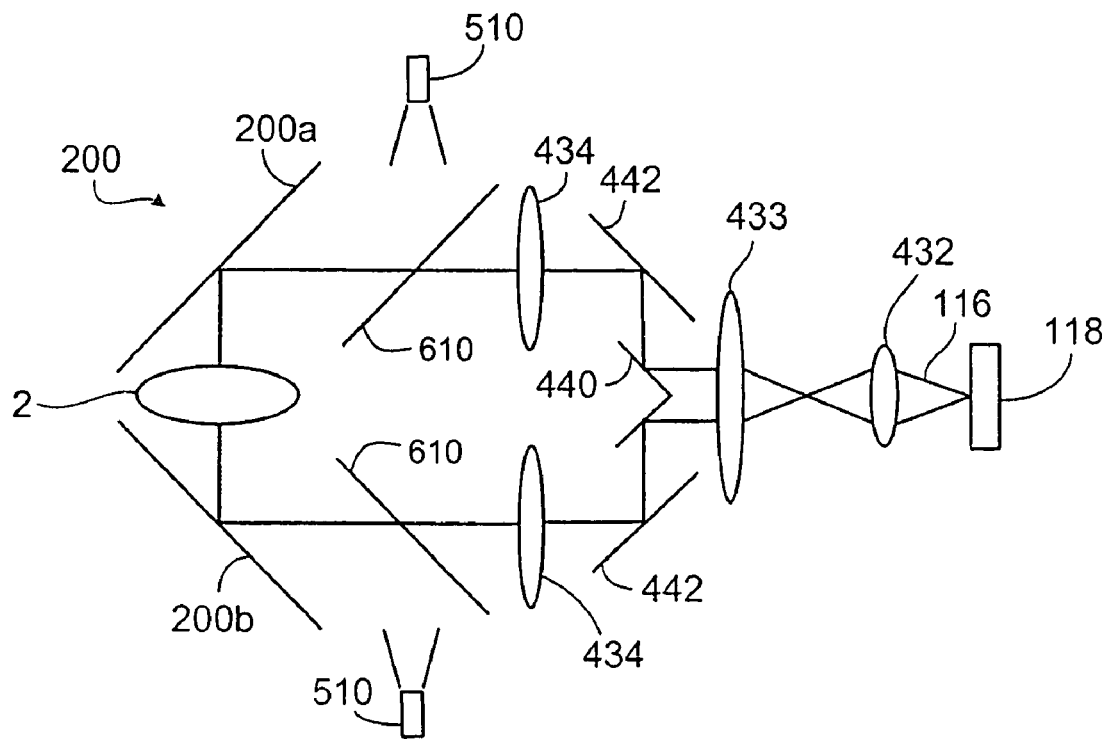
FIG. 14 is a schematic diagram showing an embodiment of a measurement system that includes a structured illumination source.

FIG. 14 shows another embodiment of a measurement system in which optical fiber bundles 510 are used together with dichroic beamsplitters 610 to direct structured illumination light onto specimen 2 from selected directions. Fluorescence radiation emitted by specimen 2 in response to the illumination light is red-shifted and is therefore transmitted by beamsplitters 610 and eventually detected by detector system 118. The optical fiber bundle source elements 510 may all provide illumination light simultaneously, or source elements 510 may be turned on and off to provide direction-sequential illumination of specimen 2.

Figure 15:
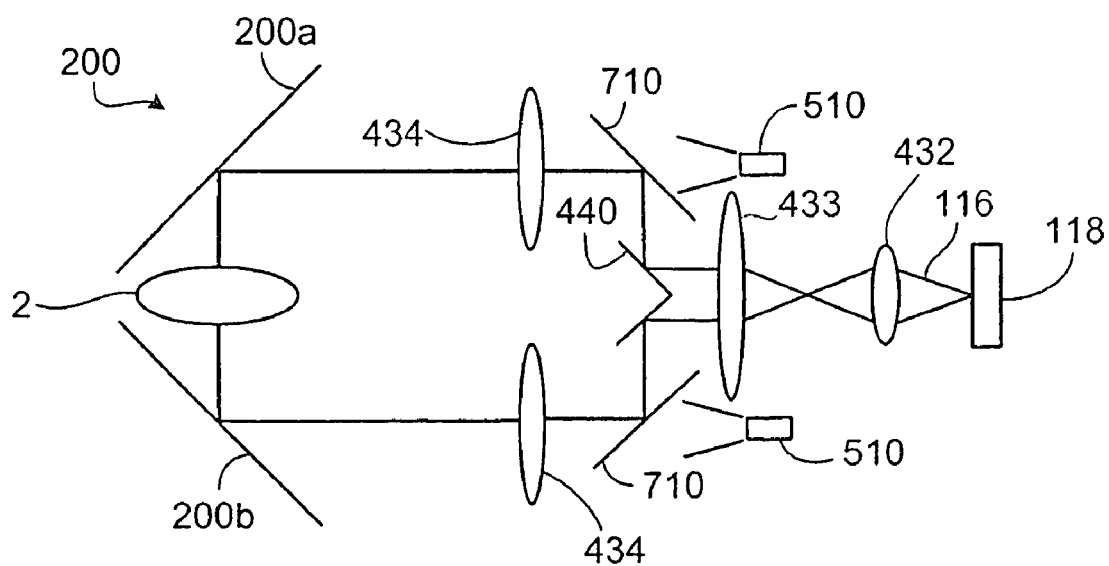
FIG. 15 is a schematic diagram showing an embodiment of a measurement system that includes a structured illumination source.

Yet another embodiment is shown in FIG. 15, wherein light from fiber bundles 510 is transmitted through dichroic beamsplitters 710 and directed by surfaces 200a and 200b of pyramid 200 to impinge upon specimen 2. Fluorescence emitted by specimen 2 is reflected by dichroic beamsplitters 710 and captured as multiple views 116 of specimen 2 by detector system 118.

In a second aspect, structured illumination may be provided by combining some or all of the light source elements in an illumination system with one or more additional optical elements configured to modify the spatial intensity distribution of the illumination light source elements. For example, in FIG. 13, each of the fiber bundle source elements 510 may be used in combination with image-forming optics and one or more optical elements such as diffractive elements, spatial masks, or spatial light modulators (e.g., MEMS digital light processors, liquid crystal modulators), or the like in order to modulate the spatial distribution of light emanating from each of the fiber bundles. Source element interference effects can also be used to produce a composite illumination source having a modulated spatial intensity profile. Further, this aspect can be combined with the previous structured illumination and direction-sequential aspects to produce an illumination source that provides structured and direction-sequential illumination, wherein individual source elements in a structured and/or direction-sequential source can have an output intensity profile with a chosen modulation.

Figure 16:
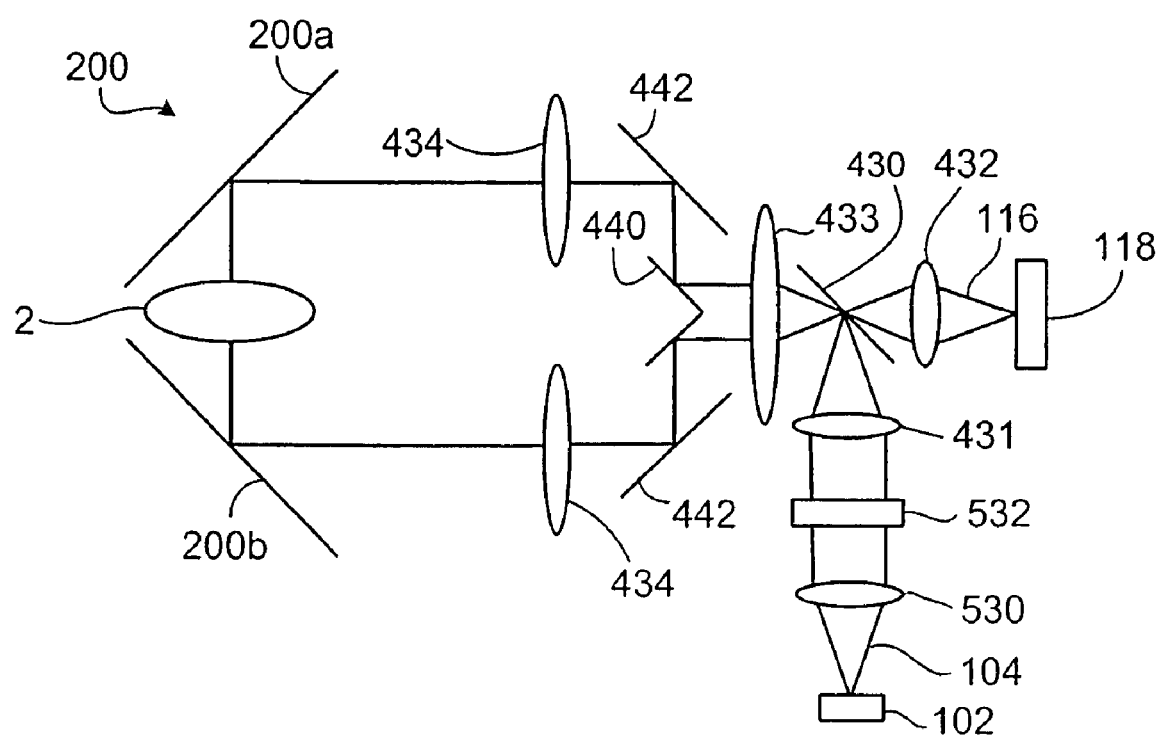
FIG. 16 is a schematic diagram showing an embodiment of a measurement system that includes a structured illumination source and a spatial light modulator.

In some embodiments where a passive or active optical device is used to modulate the intensity profile of a light source element, the surface of the optical device can be imaged by one or more imaging lenses onto the surface of a specimen. For example, FIG. 16 is a schematic diagram of a system that provides for structured illumination of specimen. Many of the elements of FIG. 16 are similar to those of FIG. 12. In addition, FIG. 16 includes a spatial light modulator 532 positioned and configured to modify the spatial intensity profile of light 104 provided by source 102. Lenses 530, 431, 433, 434, and 439 are positioned to image the surface of spatial light modulator 532 onto specimen 2, providing for configurable, patterned illumination on multiple sides of the specimen. In other embodiments, spatial light modulator 532 can be positioned in another imaging relationship to the specimen, such as in a conjugate image plane.

Generally, two- or three-dimensional implementations of the embodiments shown in FIGS. 13-15 can also include one or more spatial light modulators, masks, diffractive optics, or other devices that modify the spatial intensity profile of one or more light source elements. The surfaces of these devices can also be imaged by a set of imaging lenses onto the surface of a specimen, as described above for FIG. 16, or the devices can be positioned in another imaging relationship to the specimen, such as in a conjugate image plane.

In general, structured illumination modes of operation can be used to acquire additional information about a specimen that is not available using a standard unmodulated illumination source. Structured illumination can be used to illuminate a specimen from a single direction or from any number of multiple directions, simultaneously or in sequential fashion. Structured illumination can further be used in combination with any of the measurement modes discussed previously in order to extract additional information about the specimen under study. For example, structured illumination can be used to provide profile or topographic information about a specimen by illuminating selected regions of the surface of the specimen. In some embodiments, illumination light is focused by light conditioning optics 106 to a spot having a small diameter (relative to the size of the specimen) in a focal plane positioned to coincide with the surface of the specimen. The position of the focal plane can then be adjusted by reconfiguring light conditioning optics 106 or by translating the specimen using illumination stage 110. By capturing multiple images of the illumination spot on the specimen surface for different focal plane positions, the position of "best focus" can be measured since the depth of focus of light conditioning optics 106 is limited. As an example, the position of best focus may correspond to a focal plane position that produces a smallest measured spot diameter on an image of the specimen surface. By performing similar measurements at other positions on the surface of the specimen, a series of "best focus" focal plane positions is determined, and these correspond to a surface topographic map or height profile of the specimen.

In addition, single or multiple views that include radiation emitted from the specimen, such as fluorescence radiation, in response to structured illumination can be captured by detector system 118.

Structured illumination patterns can include, for example, arrays of illumination points overlaying the surface of a specimen, a single illumination point scanned over the surface of a specimen, an illumination grid, and in general, any other desired structured illumination pattern. In general, an operator of measurement system 100 can selectively illuminate the entire surface of specimen 2 or any portion thereof, in simultaneous fashion or in a direction-sequential modality.

Depth and/or tissue thickness information for labeled subsurface structural entities internal to a specimen can be obtained via structured illumination in the same manner as for the multiple wavelength illumination and multiple wavelength emission measurement modes discussed previously. For example, illumination of a specimen in a selected region, followed by measurement of specimen fluorescence by capturing multiple specimen views 116 using light collecting optics 114 and detector system 118, can be used in order to determine the amount of tissue through which emitted fluorescence radiation propagates in each of the views, thereby establishing the internal position of the illuminated portion of the structural entity of interest.

Alternatively, or in addition, direction-sequential structured illumination in selected regions of the specimen surface and imaging of the emitted fluorescence or scattered light can be used together with turbid media scattering models to determine surface topographic features of the emitting or scattering entity.

Figure 17:
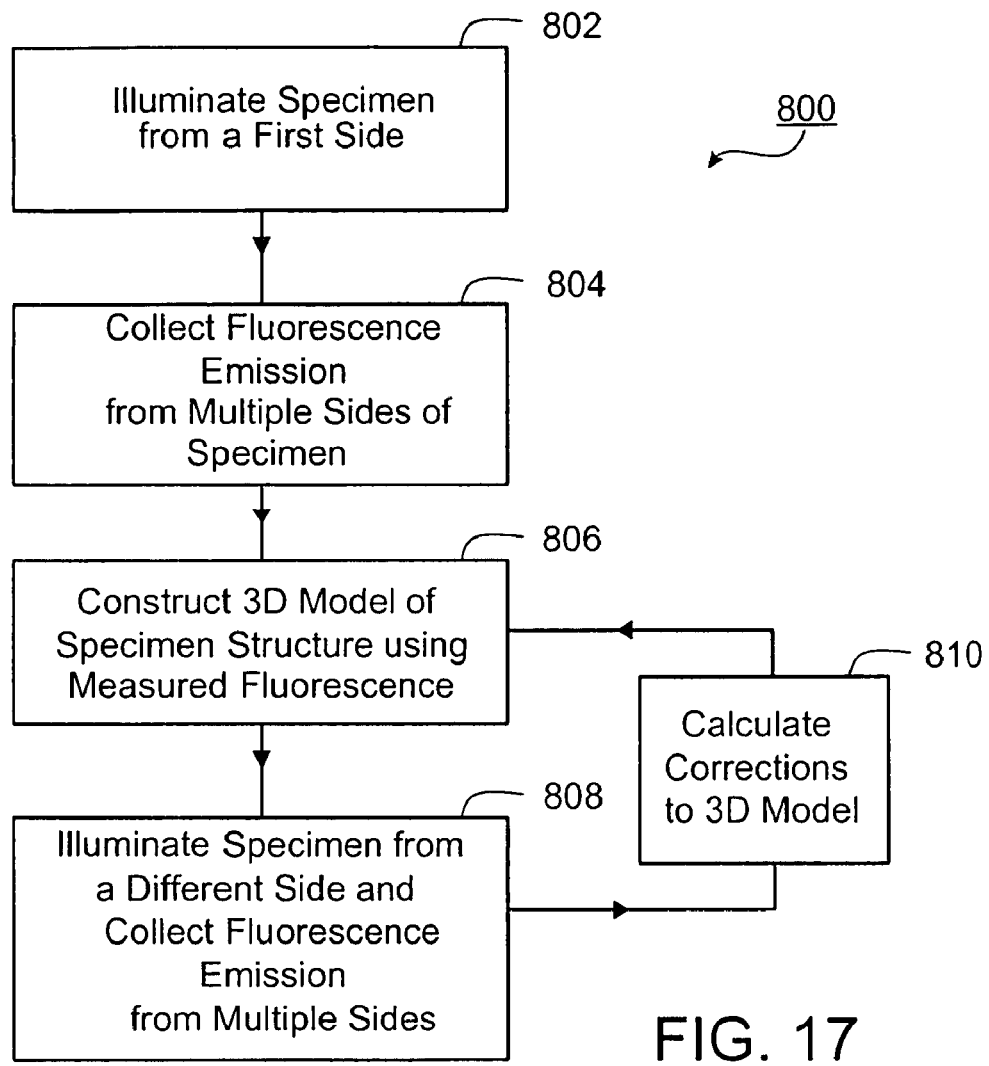
FIG. 17 is a flow chart that includes steps for refining a 3D specimen model using measurement data acquired from structured illumination of the specimen.

FIG. 17 is a flow chart 800 showing steps involved in a structured illumination measurement, where the information gained is used to as input to a 3D reconstruction model. In a first step 802, a specimen having one or more fluorescence-labeled internal structural entities of interest is illuminated on a chosen first side using a structured illumination source. In step 804, fluorescence radiation emitted by the labeled specimen is collected from multiple sides of the specimen using light collecting optics 114 and detector system 118. The light collecting optics can include, for example, a multi-faceted pyramid such as pyramid 200, along with lenses, mirrors, and other optical elements. The light from multiple sides of the specimen can be imaged as a set of views of the specimen on a CCD detector, for example. The information contained in the multiple fluorescence images is used as input to a 3D reconstruction algorithm in step 806, where the algorithm produces a 3D model of the internal structure of the specimen. In order to further refine the model, in step 808, a second side different from the first side is selected and illuminated, and fluorescence radiation emitted by the specimen due to illumination on the second side is collected on multiple sides of the specimen. The information in the new set of fluorescence images is extracted and used as input to the 3D reconstruction algorithm in step 810 to generate corrections to the 3D model of the specimen's structure. These corrections are used in step 806 to generate an improved 3D specimen model. Steps 808, 810, and 806 then continue in cyclic fashion in order to self-consistently improve the calculated 3D structure model, on each iteration choosing a different side for specimen illumination. The algorithm can be interrupted when the model is sufficiently detailed or accurate, or when successive iterations no longer produce significant changes in structure or accuracy.

Direction-sequential and structured illumination of a specimen and multiple captured views of the specimen undergoing fluorescence or light scattering can also provide complementary information for 3D reconstruction algorithms. For example, direction-sequential illumination can be used to perform time-of-flight fluorescence measurements on a specimen. In specimens where an internal fluorescing entity such as a tumor is asymmetrically positioned with respect to a nominal axis of the specimen, the temporal dependence of the fluorescence emitted by the specimen in multiple views of the specimen may vary, providing information about absorption and scattering of illumination light by specimen tissues.

In another aspect, structured illumination can be used to prevent illumination light from being directed to the eyes of a biological specimen. For example, mice are commonly used specimens in fluorescence imaging studies, and when anaesthetized, the eyelids of mice often do not fully close. The relatively intense light sources used to induce fluorescence in specimens such as mice could conceivably exceed permissible exposure levels, or induce involuntary nervous responses in mice such as twitching or other movements that reduce the reproducibility and accuracy of measured data. Structured illumination provides a means for avoiding these consequences. In some embodiments, for example, one or more modulating elements such as masks, spatial light modulators (e.g., MEMS digital light processors, liquid crystal modulators), and the like may be used in conjunction with light source 102 to reduce the intensity of illumination light that is incident on the surface of the specimen in the vicinity of the specimen's eyes in order to reduce the likelihood of causing a nervous response.

Figure 18:
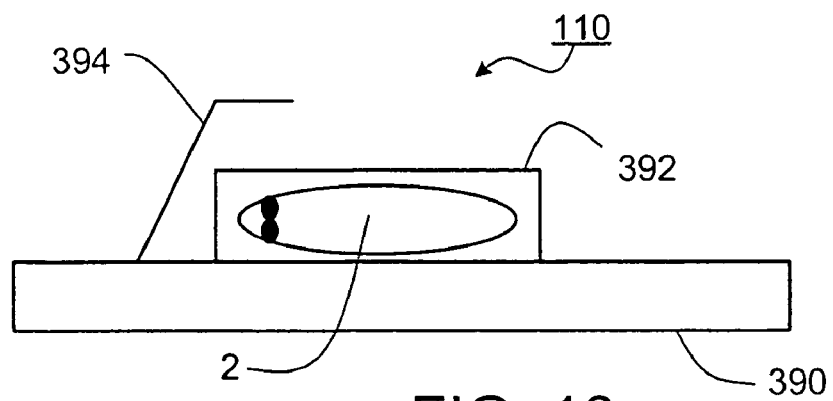
FIG. 18 is a schematic diagram of an embodiment of an illumination stage with a shield to prevent incident radiation from impinging upon the eyes of a specimen.

In some embodiments, for example, illumination stage 110 can be provided with a shield to prevent exposure of the specimen's eyes to illumination light. FIG. 18 shows an embodiment of illumination stage 110 that includes a support platform 390 and a specimen holder 392. Light shield 394 includes an optically opaque light block affixed to a rotatable and extendible arm so that the light block can be configurably positioned over the eyes of a specimen such as a mouse in order to prevent illumination light from reaching the specimen's eyes. Other embodiments of light shield 394 are possible. For example, light shield 394 can be implemented as a movable shield affixed to specimen holder 392. Alternatively, for example, light shield 394 can be incorporated into support platform 390, with the specimen in specimen holder 392 positioned relative to platform 390 such that light shield 394 prevents illumination light from entering the eyes of the specimen.

General Measurement System Components

Each of the operating modes of measurement system 100 have been discussed with reference to specific embodiments and configurations of the measurement system. However, it is important to recognize that in general, many different configurations and operating modes of the measurement system are possible, and different operating modes can be used in combination or in complementary fashion.

Similarly, although some specific elements of measurement system 100 have already been discussed, it should be recognized that measurement system 100 can, in general, include any or all of a wide variety of optical elements and components. The determination of suitability of any particular component rests with the operator of the measurement system, and is typically made based on the nature, accuracy, and reproducibility of measurements made with the system. In view of the foregoing, in this section we summarize the different optical and other components that may be included in measurement system 100.

In general, light source 102 can include one or more light source elements configured to provide light 104. Light source 102 can include a single light-producing element such as a metal halide lamp, a xenon arc lamp, a light-emitting diode, or a laser. Alternatively, light source 102 can include any combination of multiple light-producing elements suitable for a particular measurement mode.

Light source 102 can provide illumination light in the ultraviolet, visible, infrared, or another region of the electromagnetic spectrum. In some embodiments, the light provided by light source 102 can have a relatively wide spectral distribution. For example, light source 102 can have a full-width half-maximum (FWHM) spectral distribution of about 20 nm or greater. In other embodiments, for example, light source 102 can have a narrower spectral distribution, such as a spectral distribution with FWHM less than about 20 nm (e.g., less than about 5 nm). In some embodiments, light source 102 can be a white light source, and can have a very wide spectral distribution covering substantially all of the visible region of the spectrum.

Light 104 can be provided in the form of a light beam, such as a laser beam, or can have a more diffuse spatial intensity profile, such as for a lamp.

In some embodiments, light source 102 can include two or more light-producing elements providing light at the same or different wavelengths. For example, embodiments may feature a light source 102 that includes a first source element that produces reference illumination light, the reference illumination light including a broad distribution of wavelengths (i.e., white light), and a second source element that produces measurement illumination light having a relatively narrow distribution of wavelengths. The reference light can be used to illuminate a specimen for purposes of visualization during positioning, or surface profilometry, or 3D modeling. The measurement source can be used to illuminate the specimen to induce fluorescence emission, or to measure tissue absorption, scattering, or transmission. Light source 102 may further provide for selective illumination of a specimen using only a subset of source elements. For example, if light source 102 includes both white light and fluorescence source elements, one element can be used while the other is disabled.

In other embodiments, for example, light source 102 can include two or more source elements having different central wavelengths for use in multiple wavelength excitation modes of measurement. A similar light source can be provided by using a single, broadband light source element in combination with spectral filters in either light source 102 or as part of light conditioning optics 106.

In some embodiments, light source 102 can include multiple source elements providing light of nominally the same wavelength. For example, light source 102 can include multiple fiber optic sources (e.g., 3 or more fiber optic sources, 4 or more fiber optic sources, 5 or more fiber optic sources, 10 or more fiber optic sources) arranged to illuminate a specimen. The number and spatial distribution of light sources can be selected to provide a chosen spatial illumination profile.

Light source 102 can also include one or more filters, such as barrier filters, bandpass filters, or liquid crystal filters, in order to produce light 104 having a selected distribution of wavelength components.

Light conditioning optics 106, in general, include various types of optical elements for modifying the properties of light 104 provided by light source 102. For example, light conditioning optics 106 can include one or more lenses to focus and/or collimate light, e.g., to focus illumination light to a position on the surface of a specimen. Light conditioning optics 106 can also include mirrors, beamsplitters, dichroic beamsplitters, and the like. Dichroic beamsplitters can be particularly advantageous in embodiments where illumination light 108 and emitted light 112 travel along optical paths that are substantially collinear, such as in epi-fluorescence measurement systems. Dichroic beamsplitters can be used, for example, to permit spatial separation of the emitted and illumination light.

Light conditioning optics 106 can also include one or more filters such as bandpass filters, barrier filters, graded filters, epi-fluorescence filters, and/or liquid crystal filters. Filters can be used in combination, and can be mounted in a filter wheel. Filters are generally used to control the spectral properties of illumination light 108. For example, one or more filters can be used to eliminate from illumination light 108 spectral components at one or more specimen fluorescence wavelengths.

In some embodiments, light conditioning optics 106 can include one or more optical elements for controlling the spatial intensity profile of illumination light 108. For example, light conditioning optics 106 can include one or more spatial light modulators, spatial aperture masks, diffractive optical elements, or other elements configured to modulate the spatial intensity distribution of illumination light 108. Examples of spatial light modulators include MEMS digital light processors (Texas Instruments DLP Products, 6550 Chase Oaks Blvd., Plano Tex. 75023) and liquid crystal light modulators. In addition, other effects such as multi-point source element interference can be used to induce modulations in the spatial profile of illumination light 108.

For certain applications, the position of a specimen relative to a focal plane of illumination light 108 may be important. More particularly, it may be desirable in some applications to ensure that the specimen is positioned in the focal plane of the illumination light. One means of ensuring the correct positioning of the specimen is provided by configuring light conditioning optics 106 to produce structured illumination light 108 as a grid or other regular array pattern incident on a surface of the specimen. The position of the specimen with respect to one or more focusing optical elements can then be adjusted in order to ensure that the spatial intensity profile of illumination light 108 is focused with sufficient sharpness at the surface of the specimen. The spatial intensity profile of illumination light 108 can be imaged at a number of specimen positions, and the optimum specimen position can be chosen from among the measurement positions or interpolated.

Spatial light modulators and other optical devices and elements for modifying the spatial intensity profile of illumination light 108 can also be used to provide more spatially uniform illumination of a specimen where desired in some embodiments. For example, these modulating elements can be used to provide a more uniform illumination profile from a single optical source element by correcting for center-edge intensity fall-off. Alternatively, or in addition, modulating elements can be used to produce a composite light source 102 that includes multiple light source elements, wherein the modulating elements are operated in tandem in order to smooth the spatial intensity profile of composite source 102.

In general, a specimen of interest is mounted on illumination stage 110, and illumination light is directed to be incident thereon. Illumination stage 110 can include a specimen holder, for example, secured to a supporting platform. The supporting platform can be affixed to a translation stage that provides illumination stage 110 with multiple degrees of translational freedom. The position of illumination stage 110 can be changed in response to an automated signal from electronic control system 122, for example, or in response to a manual signal from an operator. In some embodiments, adjustment of the position of the specimen relative to the imaging system can also be accomplished by adjusting the positions of the light conditioning optics and the light collecting optics while illumination stage 112 remains in the same position. In this way, the positions of the focal plane of illumination light 108 and the object plane of the light collecting optics 114 can be changed independently from one another.

The specimen holder 392, illustrated schematically in FIG. 18, may in general be any type of support structure, holder, or mount capable of supporting a specimen for study. The specimen holder should generally permit illumination light 108 to be incident on the surface of the specimen, and should also permit emitted light 112 to emanate from specimen 2. The optical paths of both the illumination and emitted light should be relatively unobstructed by the specimen holder. Further, specimen holder 392 may be positioned in any orientation with respect to support platform 390.

For example, in some embodiments, the specimen holder can include several posts (e.g., 4 posts, 5 posts, 6 posts) arranged with axes parallel to one another to form a substantially regularly-shaped specimen area therebetween. For instance, a specimen holder that includes 4 posts may have a substantially rectangularly-shaped specimen area.

In other embodiments, the specimen holder may take the form of a case made from a material that is substantially transparent to the measurement light used. For example, the specimen holder can be a glass case in the shape of a cylinder. The case can be airtight, and may therefore be able to accommodate anaesthesia apparatus for immobilizing a specimen. A sealed case also prevents contamination of optical surfaces in the measurement system due to the presence of the specimen. A glass case may also be autoclavable for sterilization purposes and exhibit a low autofluorescence emission signal.

In further embodiments, the specimen holder can simply include one or more straps affixed to a base of the illumination stage to secure the specimen in place.

Generally, it is desirable to construct the specimen holder such that it is optically non-perturbative to both illumination and emitted light. For example, the specimen holder can be constructed from materials that are substantially transparent to radiation at the wavelengths of the illumination and emitted light (i.e., fluorescence emission, scattered light). By filling air spaces inside the specimen holder with an index-matching fluid, the specimen holder can further be used to define the index of refraction boundary conditions for one or more 3D reconstruction algorithms, which may improve the accuracy of the reconstructed specimen profile.

Light emitted from a specimen, e.g., fluorescence emission from internal structural entities labeled with fluorescent moieties, is captured by light collecting optics 114. In particular, the optical elements of light collecting optics 114 are configured to capture one or more views 116 of the specimen and transmit the multiple views to detector system 118.

In some embodiments, such as epi-fluorescence measurement systems for example, some optical elements may be common to both light collecting optics 114 and light conditioning optics 106. For example, light collecting optics 114 can include optical elements such as lenses, mirrors, wavelength-neutral beamsplitters, dichroic beamsplitters, and the like, some of which can be common to light conditioning optics 106.

Light collecting optics 114 can also include filter elements such as bandpass filters, barrier filters, liquid crystal filters, and interference filters. The filters may, for example, be used in some embodiments to spectrally resolve multiple views of the specimen for applications such as autofluorescence removal. In particular, filters can be used to separate spectral components in one or more views that include multiple spectral components (e.g., 2 or more spectral components, 3 or more spectral components, 10 or more spectral components).

Generally, a wide variety of 3D models can be implemented in computer programs constructed using standard programming techniques and running on a processor within electronic control system 122. Electronic control system 122 can include a processor or processing unit, a user interface such as a keyboard and a monitor, and a display device. Programs stored on computer readable media can be transferred into electronic control system 122, and when executed, may cause the processor to carry out the steps of analyzing the measurement information provided to electronic control system 122 by detector system 118. Electronic control system 122 can further be configured to display one or more views or images of the specimen under study on the display device. Electronic control system 122 can also implement algorithms for computing goodness-of-fit metrics for use in positioning mode.

Electronic control system 122 can be configured to generate one or more control signals either automatically or in response to input from an operator. For example, electronic control system 122 can generate electronic signals for translating optical components (e.g., light conditioning optics 106 and/or light collecting optics 114), for translating illumination stage 112, for capturing images with detector system 118, for time-gating detector system 118, for controlling light source elements in source 102, and for the mechanical and electronic control of other measurement system components and elements.

Although certain preferred embodiments described above involve the measurement of multiple views of a specimen, measurement systems configured to acquire only a single view or to collect light emitted by a specimen from a single side can also implement many of the described measurement techniques. For example, techniques for positioning a specimen using a reference image, for using structured illumination (including using a structured illumination source that is configured to reduce illumination in the vicinity of the specimen's eyes), and spectral fluorescence measurements using multiple excitation wavelengths and/or multiple different fluorescence labels, can all be implemented with single view detection schemes. Detector systems can be positioned to collect light emitted in any direction from a specimen, such as in a reflected or transmitted direction relative to the direction of incidence of illumination light, or in another direction.

A number of embodiments of the invention have been described. Nevertheless, it will be understood that various modifications may be made without departing from the spirit and scope of the invention. Accordingly, other embodiments are within the scope of the following claims.

What is claimed is:

1. A method comprising:
    collecting radiation emitted from an object embedded in a biological sample with optics positioned at multiple sides of the sample; and
    estimating the size of the object based on the collected radiation wherein the collected radiation is used to determine an index for a flux of emitted radiation from the object with an electronic processor coupled to a detector, and wherein the size of the object is estimated using the electronic processor based on the index and calibration information that correlates the index to the object size.

2. The method of claim 1, wherein collecting the radiation comprises collecting radiation emitted from the object through substantially all surfaces of the sample.

3. The method of claim 1, wherein the collected radiation is only a fraction of a total flux of radiation emitted from the object through substantially all surfaces of the sample.

4. The method of claim 1, wherein the index is determined by integrating the radiation collected from the multiple sides of the sample.

5. The method of claim 1, wherein the object is spaced from all of the surfaces of the sample by more than a millimeter.

6. The method of claim 1, wherein the emitted radiation is fluorescence or bioluminescence.

7. The method of claim 1, wherein the object is a tumor and the sample is an animal.

8. The method of claim 1, wherein the object is labeled with a compound that causes the emitted radiation to be in a selected range of wavelengths.

9. The method of claim 1, wherein estimating the size of the object comprises integrating the collected radiation and estimating the size of the object based on the integrated radiation.

10. The method of claim 9, wherein the estimating further comprises estimating the mass of the object from the integrated radiation and estimating the size of the object based on the estimated mass of the object.

11. The method of claim 10, wherein the estimating further comprises determining spatially resolved information about the sample from at least some of the collected information and using the spatially resolved information to improve the estimation of the size of the object.

12. The method of claim 1, wherein collecting the emitted radiation comprises using spectral unmixing techniques to remove autofluorescence from the sample.

13. The method of claim 12, wherein using the spectral unmixing techniques comprises measuring the relative intensity of the collected radiation at two or more emission wavelengths, using the measured relative intensities of the collected radiation at the two or more emission wavelengths to adjust the relative intensities to account for autofluorescence, and using the adjusted intensities to estimate the size of the embedded object.

14. The method of claim 13, wherein the accounting for the autofluorescence is based on a linear decomposition of the measured intensities in terms of spectral signatures for the object and one or more other components of the sample.

15. The method of claim 1, further comprising illuminating the sample to induce the emission of the radiation from the object.

16. The method of claim 1, wherein collecting the radiation emitted from the object from the multiple sides of the sample comprises imaging the radiation emitted through each side of the sample to a detector system.

17. The method of claim 16, wherein an optical element having multiple reflective surfaces is used to image the multiple sides of the sample to the detector system.

18. The method of claim 1, wherein the collected radiation processed by the electronic processor is collected sequentially for each of the multiple sides of the object.

19. A system comprising:
    optics for collecting radiation emitted from an object embedded in a biological sample from multiple sides of the sample;
    a detector system for receiving the radiation collected by the optics; and
    an electronic processor coupled to the detector for estimating the size of the object based on the collected radiation, wherein the electronic processor is configured to use the collected radiation to determine an index for a flux of radiation emitted from the object, and estimate the size of the object based on the index and calibration information that correlates the index to the object size.

20. The system of claim 19, wherein the collecting optics are configured to collect radiation emitted from the object through substantially all surfaces of the sample.

21. The system of claim 19, wherein the collecting optics are configured to collect only a fraction of a total flux of radiation emitted from the object through substantially all surfaces of the sample.

22. The system of claim 19, wherein the electronic processor is configured to determine the index based on integrated radiation collected from the multiple sides of the sample.

23. The system of claim 19, further comprising a mount to secure the biological sample relative to the optics.

24. The system of claim 19, further comprising an illumination source.

25. The system of claim 19, wherein the collecting optics comprise a pyramidal arrangement of mirrors and an imaging lens.

26. The system of claim 19, wherein the detector system is a multi-element detector.

27. The system of claim 19, wherein the detector system comprises multiple detectors corresponding to different sides of the sample.

28. The system of claim 19, wherein the detector system is configured to measure the relative intensity of the collected radiation at two or more emission wavelengths, and wherein the processor is configured to adjust the measured relative intensities of the collected radiation at the two or more emission wavelengths to adjust for autofluorescence from the sample and use the adjusted intensities to estimate the size of the embedded object.

29. The system of claim 28, wherein the processor is configured to adjust for the autofluorescence based on a linear decomposition of the measured intensities in terms of spectral signatures for the object and one or more other components of the sample that produce the autofluorescence.

30. The method of claim 13, wherein the two or more emission wavelengths comprise 3 or more emission wavelengths.

31. The method of claim 13, wherein the two or more emission wavelengths comprise 4 or more emission wavelengths.

32. The system of claim 28, wherein the two or more emission wavelengths comprise 3 or more emission wavelengths.

33. The system of claim 28, wherein the two or more emission wavelengths comprise 4 or more emission wavelengths.

34. The method of claim 8, wherein the emitted radiation is in the near-infrared range.

35. The method of claim 34, wherein the emitted radiation is in the range of 700-900 nm.

36. The system of claim 19, wherein the detector system is configured to measure emitted radiation in the near-infrared range.

37. The system of claim 36, wherein the near-infrared range is in the range of 700-900 nm.

38. The system of claim 19, wherein the collected radiation processed by the electronic processor is collected sequentially for each of the multiple sides of the object.

* * * * *

UNITED STATES PATENT AND TRADEMARK OFFICE
CERTIFICATE OF CORRECTION

PATENT NO.       : 7,477,931 B2                              Page 1 of 1
APPLICATION NO.  : 11/295140
DATED            : January 13, 2009
INVENTOR(S)      : Clifford C. Hoyt It is certified that error appears in the above-identified patent and that said Letters Patent is hereby corrected as shown below:

On the Title Page, Item
(54) Title, before "OPTICAL" delete "AND"
(74) Attorney, delete "FIsh & Richardson P.C." and insert --Fish & Richardson P.C.--

Column 1
Line 2, before "OPTICAL" delete "AND"

Signed and Sealed this

Thirty-first Day of March, 2009

JOHN DOLL
*Acting Director of the United States Patent and Trademark Office*